(12) United States Patent
Peng et al.

(10) Patent No.: US 10,670,598 B2
(45) Date of Patent: Jun. 2, 2020

(54) PREPARATION METHOD OF CRYPTOCOCCUS NEOFORMANS CAPSULAR POLYSACCHARIDE GXM AS WELL AS GXM ANTIGEN IMMUNOASSAY KIT AND APPLICATION THEREOF

(71) Applicant: DYNAMIKER BIOTECHNOLOGY (TIANJIN) CO.,LTD, Tianjin (CN)

(72) Inventors: Jie Peng, Tianjin (CN); Dongdong Shi, Tianjin (CN); Ning Li, Tianjin (CN); Yan Su, Tianjin (CN); Zeqi Zhou, Tianjin (CN)

(*) Notice: Subject to any disclaimer, the term of this patent is extended or adjusted under 35 U.S.C. 154(b) by 6 days.

(21) Appl. No.: 15/924,170

(22) Filed: Mar. 16, 2018

(65) Prior Publication Data

US 2018/0209974 A1 Jul. 26, 2018

Related U.S. Application Data

(63) Continuation of application No. PCT/CN2017/074700, filed on Feb. 24, 2017.

(30) Foreign Application Priority Data

| Feb. 29, 2016 | (CN) | 2016 1 0112315 |
| Feb. 29, 2016 | (CN) | 2016 1 0112389 |
| Feb. 29, 2016 | (CN) | 2016 1 0112390 |

(51) Int. Cl.
| C08H 1/00 | (2006.01) |
| G01N 33/569 | (2006.01) |
| C12P 19/04 | (2006.01) |
| G01N 30/02 | (2006.01) |
| B01D 15/38 | (2006.01) |
| C08B 37/00 | (2006.01) |
| G01N 33/535 | (2006.01) |

(52) U.S. Cl.
CPC ... *G01N 33/56961* (2013.01); *B01D 15/3809* (2013.01); *C08B 37/0003* (2013.01); *C12P 19/04* (2013.01); *G01N 30/02* (2013.01); *G01N 33/535* (2013.01); *G01N 2333/39* (2013.01)

(58) Field of Classification Search
None
See application file for complete search history.

(56) References Cited

FOREIGN PATENT DOCUMENTS

CN 102952201 A 3/2016

OTHER PUBLICATIONS

International search report of PCT/CN2017/074700, dated May 8, 2017.
Rodrigues, M.L. et.al.; Vesicular Polysaccharide Export in Cryptococcus neoformans is a Eukaryotic Solution to the Problem of Fungal Trans-Cell Wall Transport. Eukaryotic Cell; vol. 6, No. 1; Jan. 31, 2007; p. 49; left-hand volume,the last paragraph to right-hand column,paragraph 1.
De Ruiter, G.A. et.al; Detection of fungal carbohydrate antigens by high-performance immunoafnity chromatography using a protein A column with covalently linked immunoglobulin G.; Journal of Chromatography.; vol. 584, Dec. 31, 1992; pp. 69-75.
Murphy.J.W. et.al; Induction of antigen-specific suppression by circulating Cryptococcus neoformans antigen.; Clin. Exp.Immunol; vol. 73; Dec. 31, 1988;pp. 174-180.
Andrade, R.M. et.al,Glucuronoxylomannan of Cryptococcus neoformans exacerbates in vitro yeast cell growth by interleukin 10-dependent inhibition of CD4+ T lymphocyte responses; Cellular Immunology; vol. 222, Dec. 31, 2003; pp. 116-125.

*Primary Examiner* — Jennifer E Graser
(74) *Attorney, Agent, or Firm* — Erson IP (Nelson IP)

(57) ABSTRACT

The present invention discloses a preparation method of *Cryptococcus neoformans* capsular polysaccharide GXM as well as a GXM antigen immunoassay kit and an application thereof. The preparation method of the *Cryptococcus neoformans* capsular polysaccharide GXM effectively avoids the use of a toxic chemical reagent, ensures safety of operators, and also avoids environmental pollution, has high specificity, and can prepare a high-purity *Cryptococcus neoformans* capsular polysaccharide while simplifying a preparation process. The GXM antigen immunoassay kit adopts a competition method, has good sensitivity, specificity, repeatability and stability, has high recovery rate of a target compound and may provide more accurate and reliable inspection results. The kit is simple and feasible in use and operation, rapid and sensitive in detection and low in price and provides an effective tool for clinical detection of GXM.

12 Claims, 6 Drawing Sheets

Figure 1:
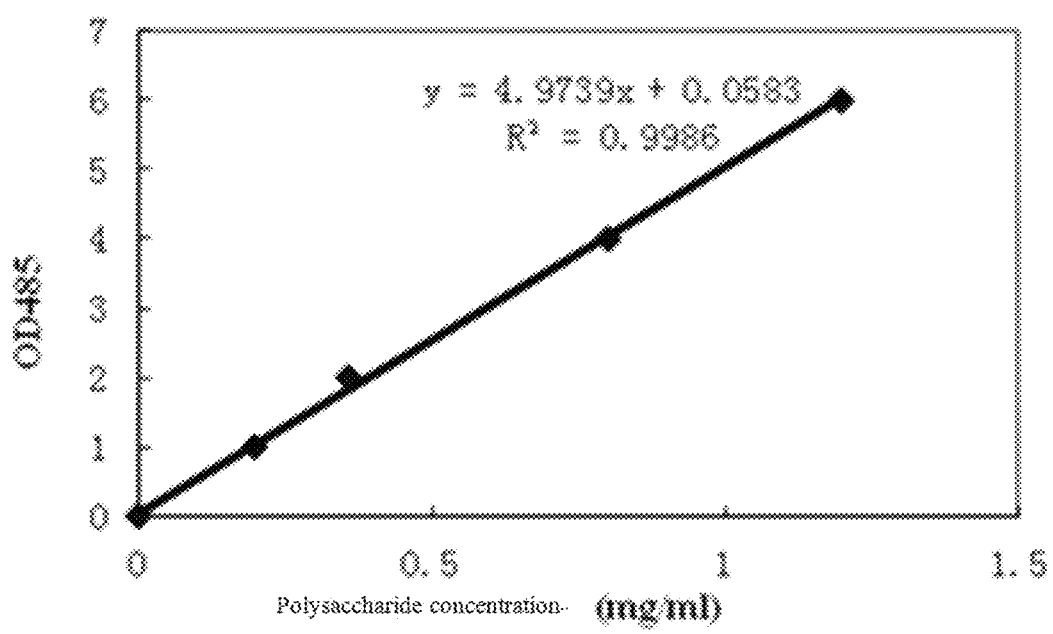
Figure 2:
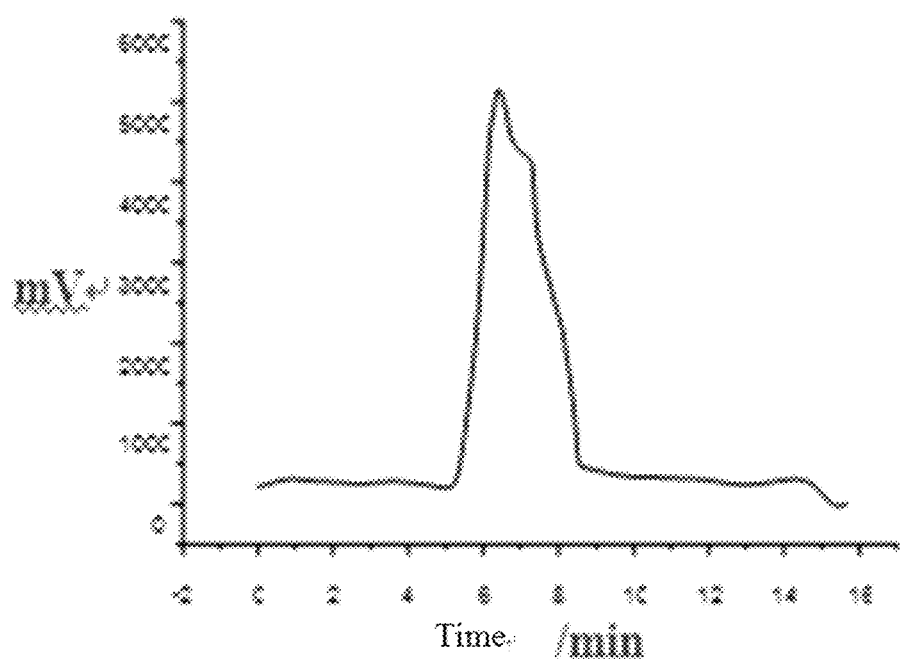
Figure 3:
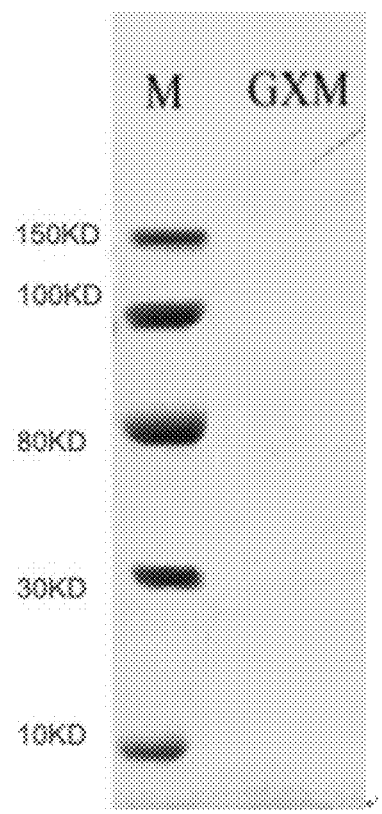

PREPARATION METHOD OF CRYPTOCOCCUS NEOFORMANS CAPSULAR POLYSACCHARIDE GXM AS WELL AS GXM ANTIGEN IMMUNOASSAY KIT AND APPLICATION THEREOF

CROSS-REFERENCE TO RELATED APPLICATIONS

This application is a continuation of International Patent Application No. PCT/CN2017/074700 with a filing date of Feb. 24, 2017, designating the United States, now pending, and further claims priority to Chinese Patent Application No. 201610112315.4 with a filing date of Feb. 29, 2016, No. 201610112389.8 with a filing date of Feb. 29, 2016, and No. 201610112390.0 with a filing date of Feb. 29, 2016. The content of the aforementioned applications, including any intervening amendments thereto, are incorporated herein by reference.

FIELD OF THE INVENTION

The present invention relates to the technical field of immunoassay, and particularly relates to a preparation method of *Cryptococcus neoformans* capsular polysaccharide GXM (glucuronoxylomannan), a polyclonal antibody and a preparation method of the polyclonal antibody with respect to the GXM antigen, and an immunoassay kit as well as a preparation method and an application thereof with respect to the GXM antigen.

BACKGROUND OF THE INVENTION

*Cryptococcus neoformans* is an important conditioned pathogen, and often infects patients with low immunocompetence or immunodeficiency, causing deep fungal infection with a principle symptom of central nervous system infection. The deep fungal infection may cause an extremely high case fatality rate. Large series of epidemiologic study performed by Center for Disease Control and Prevention (CDC) in 1992-1993 showed that an annual incidence rate of the deep fungal infection is 178.3/million, wherein the annual incidence rate of cryptococcosis is 65.5/million, accounting for about 36.7%.

In recent years, because of long-term wide applications of broad-spectrum antibacterial drugs, adrenocortical hormone, tumor chemotherapy, radiation oncology and immunosuppressors after organ transplantation as well as the epidemic of AIDS, the cryptococcosis is obviously increased. *Cryptococcus neoformans* meningitis (hereinafter referred to as cryptococcal meningoencephalitis) is the most common central nervous system disease caused by the *Cryptococcus neoformans*, and accounts for about 80% of the cryptococcosis. Due to complicated clinical manifestations and atypical symptoms, the cryptococcal meningoencephalitis is difficult to be diagnosed. About 80% of patients suffering from the cryptococcal meningoencephalitis may be misdiagnosed with tubercular meningitis.

Primary causal factors of the *Cryptococcus neoformans* are capsule, melanin, growth capability thereof in a host temperature environment, etc. The capsule is one of the main determination factors that influence toxicity of the *Cryptococcus neoformans*. A main component of the capsule is capsular polysaccharide and has the effects of inhibiting phagocytosis and activating complement, and the component with the highest content is glucuronoxylomannan (GXM). In an early diagnosis method of the *cryptococcus neoformans* meningitis, Wang et al. detect a *Cryptococcus neoformans* capsular polysaccharide antigen by adopting a latex agglutination test and evaluate diagnostic sensitivity and specificity by fungal culture and direct microscopic examination methods. Results show that the sensitivities of the latex agglutination test, the fungal culture and the direct microscopic examination are respectively 91.1%, 69.6% and 73.2%, and the specificities are respectively 96.0%, 100% and 100%. Thus, it is believed that, the latex agglutination test for detecting the *Cryptococcus neoformans* capsular polysaccharide antigen can serve as the early diagnosis method of the *cryptococcus neoformans* meningitis. The method for performing *cryptococcus* latex agglutination test on the *cryptococcus neoformans* meningitis has high specificity in diagnosis of the *cryptococcus neoformans* meningitis, so that an early diagnosis rate is increased (Wang H, Yuan X, Zhang L. Latex agglutination: Diagnose the early *cryptococcus neoformans* test of capsular polysaccharide antigen. Pakistan journal of pharmaceutical sciences, 2015, 28(1 Suppl): 307-311). Therefore, the *Cryptococcus neoformans* capsular polysaccharide is very important to early diagnosis of the *cryptococcus neoformans* meningitis.

Kozel et al. perform the following steps: culturing the *cryptococcus neoformans* in a culture tank, performing autoclaved sterilization on a culture solution, centrifuging to remove thalli, filtering the supernatant with a filter membrane of 0.45 um, performing ultrafiltration concentration, adding sodium acetate and glacial acetic acid into the concentrated solution, and precipitating a coarse capsular polysaccharide with ethanol; repeatedly extracting with chloroform/n-butyl alcohol (v:v=5:1), removing protein, precipitating the capsular polysaccharide with ethanol, centrifuging and collecting the precipitate, dissolving the precipitate in deionized water, dialyzing and freeze-drying, thereby obtaining refined capsular polysaccharide. (Kozel T R, Cazin J. Nonencapsulated variant of *Cryptococcus neoformans* I. Virulence studies and characterization of soluble polysaccharide. Infection and immunity, 1971, 3(2): 287-294). Lots of chloroform should be used in the above method. The chloroform is a toxic and harmful dangerous chemical, has carcinogenic risk and also has high requirements for operating conditions, protection of operators, sewage treatment and the like.

Bryan et al. perform the following steps: washing *cryptococcus neoformans* cells with distilled water for 3 times, centrifuging and collecting the cells, resuspending the collected wet cells with 15 mL of dimethyl sulfoxide (DMSO) and incubating for 30 minutes; precipitating and separating the cells by centrifuging, dialyzing DMSO supernatant for 12 hours, exchanging water every 2 hours, fully dialyzing the obtained sample with distilled water or 1 mM EDTA for 3 days, and performing freeze drying on a polysaccharide solution obtained by dialyzing, thereby obtaining the capsular polysaccharide (Bryan R A, Zaragoza O, Zhang T, et al. Radiological studies reveal radial differences in the architecture of the polysaccharide capsule of *Cryptococcus neoformans*. Eukaryotic Cell, 2005, 4(2): 465-475). The above method is long in preparation cycle, and the yield of the product is low.

Maxson et al. perform the following steps: centrifuging the culture fluid of the *cryptococcus* cells, separating a cell precipitate, concentrating the obtained supernatant by about 20 times by using a polyether sulfone ultrafiltration plate, continuously stirring in the concentrating process, discharging a fluid phase after a sticky film is formed on the filtration plate, recovering binding material by using a cell scraper, and finally performing freeze drying, thereby obtaining the capsular polysaccharide (Maxson M E, Dadachova E, Casadevall A, et al. Radial mass density, charge, and epitope distribution in the *Cryptococcus neoformans* capsule. Eukaryotic cell, 2007, 6(1): 95-109). The above method is simple in operation and short in preparation cycle, but the yield of the product is also low.

In addition, Frases et al. find in experiments that, extracellular polysaccharide and the capsular polysaccharide of the *cryptococcus* are structurally different, and also find in experiments that, by comparing polysaccharide prepared by precipitating through cetyl trimethyl ammonium bromide with polysaccharide prepared by concentration and ultrafiltration (see an extraction method in Maxson M E, Dadachova E, Casadevall A, et al. Radial mass density, charge, and epitope distribution in the *Cryptococcus neoformans* capsule. Eukaryotic cell, 2007, 6(1): 95-109), the mass is greater, and conformations of the polysaccharides are different. Then, it is judged that, a common method for extracting the *Cryptococcus neoformans* capsular polysaccharide may obviously influence the structure and antigenicity of the product (Frases S, Nimrichter L, Viana N B, et al. *Cryptococcus neoformans* capsular polysaccharide and exopolysaccharide fractions manifest physical, chemical, and antigenic differences. Eukaryotic cell, 2008, 7(2): 319-327).

At present, there is an urgent need to develop a preparation method of the *Cryptococcus neoformans* capsular polysaccharide with convenience, high efficiency, low cost and high specificity in the field, and the preparation method shall effectively avoid the use of any toxic and harmful chemical reagent. The present invention overcomes the defects in the prior art, provides a preparation method of *Cryptococcus neoformans* capsular polysaccharide GXM, the prepared GXM, and a detection kit prepared by utilizing the GXM. The prepared GXM has high purity and specificity. The detection kit prepared by utilizing the antigen has high detection sensitivity.

SUMMARY OF THE INVENTION

The present invention provides a preparation method of an immunoaffinity chromatography column for *Cryptococcus neoformans* capsular polysaccharide GXM. The affinity chromatography column is prepared by utilizing a monoclonal antibody of the *Cryptococcus neoformans* capsular polysaccharide GXM.

Preferably, the preparation method comprises the following steps:

(1) dissolving a monoclonal antibody of *Cryptococcus neoformans* capsular polysaccharide GXM in a solution, and mixing the monoclonal antibody with an affinity chromatography substrate to form thin homogenate;

(2) washing the homogenate obtained in the step (1) with a cross-linking buffer solution, and centrifuging to obtain a mixture of the antibody and the affinity chromatography substrate;

(3) resuspending the mixture of the antibody and the affinity chromatography substrate obtained in step (2) with the cross-linking buffer solution, adding a difunctional binding agent into the obtained suspension, incubating, uniformly mixing, and separating the liquid from the solid to obtain an affinity chromatography substrate-antibody conjugated complex;

(4) washing the affinity chromatography substrate-antibody conjugated complex obtained in the step (3) with a blocking solution to block excessive active groups in the chromatography substrate so as to terminate a cross-linking reaction;

(5) resuspending the affinity chromatography substrate-antibody conjugated complex obtained in the step (4) in the blocking solution, incubating, and uniformly mixing; and (6) packing: filling the affinity chromatography substrate-antibody conjugated complex obtained in the step (5) after successfully cross-linked when detection into a chromatographic column, thereby obtaining the immunoaffinity chromatography column for the *Cryptococcus neoformans* capsular polysaccharide GXM.

Preferably, the method further comprises a step (7) of preservation: preserving the affinity chromatography substrate-antibody conjugated complex obtained in the step (6) or the packed immunoaffinity chromatography column for the *Cryptococcus neoformans* capsular polysaccharide GXM obtained in the step (6) under a condition of 4° C., and enabling the performance to be stable within 1 year.

Preferably, the method further comprises a step (8) of regeneration: washing and regenerating the chromatography column preserved under the condition of 4° C. in the step (7) or the used chromatography column with a buffer solution which has the same solvent as a to-be-purified sample, in an amount of 10-25 times of the volume of the column bed before use.

Preferably, the affinity chromatography substrate-antibody conjugated complex obtained in the step (5) is subjected to preservative treatment and filled into the chromatography column, wherein the preservative treatment comprises the following steps: washing the affinity chromatography substrate-antibody conjugated complex obtained in the step (5) with a PBS buffer solution, resuspending the complex in the PBS buffer solution, and adding merthiolate for preservation. The concentration of the merthiolate is 0.005-0.015%.

Preferably, the affinity chromatography substrate in the step (1) is selected from protein A microbeads, protein G microbeads and active microbeads, and preferably protein A microbeads.

Preferably, the solution in the step (1) is selected from a carbonate buffer solution with a pH value of 8.0-9.0.

Preferably, a ratio of the affinity chromatography substrate to the solution in the step (1) is as follows: 0.5-2.0 mL of the affinity chromatography substrate is added into every 10 mL of the solution; a ratio of the affinity chromatography substrate to the antibody is as follows: every 1 mL of the affinity chromatography substrate is bound to 1-4 mg of the monoclonal antibody; further preferably, a ratio of the affinity chromatography substrate to the solution in the step (1) is as follows: 1 mL of the affinity chromatography substrate is added into every 10 mL of the solution; and a ratio of the affinity chromatography substrate to the antibody is as follows: every 1 mL of the affinity chromatography substrate is bound to 2 mg of the monoclonal antibody.

Preferably, the cross-linking buffer solution in the step (2) is a 0.1-0.3 mol/L of sodium borate solution with a pH value of 8.0-9.5, and the use amount of the buffer solution is 5-15 times of the volume of the affinity chromatography substrate; further preferably, the cross-linking buffer solution is a sodium borate solution with a concentration of 0.2 mol/L and a pH value of 9.0, and the use amount of the buffer solution is 10 times of the volume of the affinity chromatography substrate; and washing frequency is 1-3 times, and a centrifugal condition is to centrifuge for 2-5 minutes per 3000 g or to centrifuge for 30 seconds per 10000 g.

Preferably, the cross-linking buffer solution in the step (3) is 0.1-0.3 mol/L of sodium borate solution with pH value of 8.3-9.5, and the use amount of the buffer solution is 5-15 times of the volume of the affinity chromatography substrate; further preferably, the cross-linking buffer solution is a sodium borate solution with a concentration of 0.2 mol/L and a pH value of 9.0, and the use amount of the buffer solution is 10 times of the volume of the affinity chromatography substrate.

Preferably, the difunctional binding agent in the step (3) is selected from dimethyl heptandilate, carbonyldimidazole, cyanogen bromide, hydroxysuccinimide and acetyl iodine, and preferably the dimethyl heptandilate. The use amount of the difunctional binding agent is as follows: the final concentration of the binding agent in affinity chromatography substrate suspension is 15-25 mmol/L, and preferably 20 mmol/L.

Preferably, the blocking solution in the steps (4) and (5) is selected from ethanol amine, aminoethane and other solutions of small molecular substances containing active groups which can be bound to amino, and preferably an ethanol amine solution, further preferably an ethanol amine solution with a concentration of 0.1-0.25 mol/L and a pH value of 7.5-8.5, and more preferably 0.2 mol/L of ethanol amine solution with a pH value of 8.0.

Preferably, a detection process of cross-linking efficiency of the affinity chromatography substrate-antibody conjugated complex in the step (6) comprises the following steps: taking an affinity chromatography substrate sample and a sample obtained by cross-linking the affinity chromatography substrate and the antibody, respectively adding the samples into a LaemmLi buffer solution to boil, respectively taking out two samples equivalent to 1 mL and 9 mL, performing electrophoresis in 10% of SDS-polyacrylamide gel, and staining with Coomassie brilliant blue, wherein if a heavy chain zone (55 kDa) is present in the sample before cross-linking while absent after cross-linking, it indicates that cross-linking is successful.

Preferably, a container is rinsed with a PBS buffer solution after packing in the step (6) is completed, and the residual affinity chromatography substrate is collected. If possible, only the affinity chromatography substrate-antibody conjugated complex needed by the total GXM in a to-be-purified sample is used.

The present invention further provides an immunoaffinity chromatography column for Cryptococcus neoformans capsular polysaccharide GXM prepared by the above method.

The present invention further provides a preparation method of the Cryptococcus neoformans capsular polysaccharide GXM. The preparation method comprises a step of purifying GXM by utilizing the above GXM immunoaffinity chromatography column.

Preferably, the preparation method comprises the following steps:

(1) performing crude extraction on *Cryptococcus neoformans* capsular polysaccharide GXM; and (2) purifying a crude extract of the *Cryptococcus neoformans* capsular polysaccharide GXM by utilizing the GXM immunoaffinity chromatography column for the *Cryptococcus neoformans* capsular polysaccharide.

The crude extraction of the *Cryptococcus neoformans* capsular polysaccharide GXM comprises the following steps:

(1) culturing *Cryptococcus neoformans* until a bacteria concentration reaches a later logarithmic phase;

(2) performing autoclaved sterilization on bacterium liquid, centrifuging to remove thalli, and reserving supernatant;

(3) slowly adding calcium acetate powder into the supernatant while stirring, and adding glacial acetic acid to regulate the pH value to be acidic; and (4) adding ethanol into the solution obtained in the step (3), standing overnight at 4° C., centrifuging, removing the supernatant, drying and precipitating, thereby obtaining the crude extract of the *Cryptococcus neoformans* capsular polysaccharide GXM.

Preferably, culture conditions of *Cryptococcus neoformans* in the step (1) of performing crude extraction on the *Cryptococcus neoformans* capsular polysaccharide GXM are as follows: a culture medium is a YM bouillon culture-medium, a culture temperature is 30° C., a shake speed is 200 rpm, culture time is 32-40 hours, and a formula of the YM bouillon culture-medium is that every liter of the culture medium contains 3 g of yeast extract, 5 g of peptone, 3 g of maltose extract and 10 g of D-glucose.

Preferably, the addition amount of the calcium acetate powder in the step (3) is as follows: the final concentration of the calcium acetate powder in the supernatant reaches 2-8%, and the pH value is regulated to 4.6-5.2 by the glacial acetic acid.

Preferably, the concentration of the ethanol in the step (4) is 90-98%, and the addition amount is 2-4 times of the volume of the solution obtained in the step (3).

The step of purifying the crude extract of the *Cryptococcus neoformans* capsular polysaccharide GXM by utilizing the immunoaffinity chromatography column for the *Cryptococcus neoformans* capsular polysaccharide GXM comprises the following steps:

(1) rinsing the immunoaffinity chromatography column for the *Cryptococcus neoformans* capsular polysaccharide GXM by utilizing a buffer solution which is the same as a to-be-purified sample solution;

(2) enabling the to-be-purified sample solution to flow through the chromatography column treated in the step (1);

(3) washing the column with a binding buffer solution;

(4) washing the column with a pre-elution buffer solution;

(5) performing stepwise elution, continuously enabling an elution buffer solution to flow through the chromatography column, and collecting each component in different tubes; and (6) detecting the content of the GXM in each tube, and merging all the tubes with high concentrations.

Preferably, (7) enabling an initial buffer solution in an amount of 10-25 times of a column bed volume to flow through the chromatography column to regenerate, adding merthiolate to enable the final concentration of the buffer solution to be 0.005-0.015%, and preserving the chromatography column under the condition of 4° C.

Preferably, flow velocity of the to-be-purified sample in the step (2) is 0.5-1.5 mL/h. The flow velocity is controlled by a pump, and preferably a peristaltic pump.

Preferably, the binding buffer solution in the step (3) is selected from one of a PBS buffer solution with a pH value of 6.0-8.0, a Tris-HCl buffer solution with a pH value of 6.0-8.0 and an acetic acid-sodium acetate buffer solution with a pH value of 6.0-8.0, and preferably the PBS buffer solution with the pH value of 6.0-8.0. The use amount of the binding buffer solution in the step (3) is 10-25 times of the column bed volume, and preferably 20 times of the column bed volume.

Preferably, the pre-elution buffer solution in the step (4) is a carbonate buffer solution with a pH value of 8.5-9.5. The use amount of the pre-elution buffer solution is 10-25 times of the column bed volume, and preferably 20 times of the column bed volume.

Preferably, the elution buffer solution in the step (5) is a buffer solution with a pH of 3.0, preferably 0.1M glycine buffer solution with a pH of 3.0, a citrate-phosphate buffer solution with a pH of 3.0, a citrate-sodium citrate buffer solution with a pH of 3.0 and an acetate-sodium acetate buffer solution with a pH of 3.0. The use amount of the elution buffer solution is 0.4-0.8 of the column bed volume.

Preferably, the GXM eluant obtained in the step (6) is subjected to dialysis desalting or the pH value of the GXM eluant is regulated by a buffer solution.

The present invention provides a *Cryptococcus neoformans* capsular polysaccharide GXM prepared by the above method.

The present invention further provides applications of the immunoaffinity chromatography column for the *Cryptococcus neoformans* capsular polysaccharide GXM in purification of the *Cryptococcus neoformans* capsular polysaccharide GXM and early diagnosis of *cryptococcus neoformans* meningitis.

The present invention further provides an application of the *Cryptococcus neoformans* capsular polysaccharide GXM in an early diagnosis reagent for *cryptococcus neoformans* meningitis.

The present invention further provides a polyclonal antibody which resists *Cryptococcus neoformans* capsular polysaccharide GXM. The polyclonal antibody is prepared by the following method: immunizing animal-derived serum by taking GXM as an immunogen, and separating and purifying to obtain an antibody. A purification method is a saturated ammonium sulfate precipitation method and/or an affinity chromatography method. The immunization method may be subcutaneous injection, intrasplenic injection, intravenous injection or intraperitoneal injection. An immunizing dosage is 0.01-1 mg per animal. Immunized animals are rats, mice, guinea pigs, rabbits, chickens, sheep, horses, pigs or donkeys, and preferably rabbits.

A preparation method of the GXM polyclonal antibody comprises the following specific steps:

(1) immunizing an animal by using a GXM antigen;

(2) determining a serum titer of the immunized animal, and collecting blood from the immunized animal; and (3) performing preliminary purification by using a saturated ammonium sulfate precipitation method and/or an affinity chromatography method.

The anti-GXM polyclonal antibody prepared by the above steps may be specifically bound to GXM and is displayed as a homogenous antibody product by using SDS-PAGE. Indirect ELISA detection shows that a titer of the polyclonal antibody is greater than $1:1\times10^6$.

The present invention further provides a GXM antigen immunoassay kit for *Cryptococcus neoformans* capsular polysaccharide. The kit comprises a GXM coated enzyme-labeled carrier, an anti-GXM polyclonal enzyme-labeled antibody and a GXM standard substance.

The GXM standard substance is composed of a series of GXM solutions with different concentrations. The GXM solutions are prepared by dissolving GXM into an appropriate solvent to form GXM solutions with specific concentrations.

The GXM coated enzyme-labeled carrier is prepared by the following method:

① diluting GXM with a coating buffer solution to obtain a GXM coating solution, and adding the GXM coating solution into wells of an ELISA plate for coating;

② adding a blocking solution into the wells of the ELISA plate obtained in the step ① for blocking; and ③ removing the blocking solution from the ELISA plate obtained in the step ②, and incubating to obtain the GXM coated enzyme-labeled carrier.

Preferably, the enzyme-labeled carrier is a microwell plate or a plastic tube, and preferably the enzyme-labeled carrier is the microwell plate.

Preferably, an enzyme used for labeling is horse radish peroxidase (HRP) or alkaline phosphatase (AP), and preferably, the enzyme used for labeling is the HRP.

Preferably, the GXM standard substance at least has 3 different concentrations in a range of 0-100 ng/mL.

In a specific embodiment of the present invention, in the above antigen immunoassay kit for the *Cryptococcus neoformans* capsular polysaccharide, the GXM standard substance has 5 different concentrations marked as a, b, c, d and e respectively. The concentrations are respectively 100, 32, 10, 6.4 and 3.2 ng/mL.

Preferably, the antigen immunoassay kit for the *Cryptococcus neoformans* capsular polysaccharide further comprises a sample treatment solution, a wash concentrate, a sample diluent, a substrate solution and a stop solution.

Preferably, components and ratios of the wash concentrate, the sample diluent, the sample treatment solution, the substrate solution and the stop solution are as follows:

the wash concentrate: a phosphate buffer solution containing 0.4-1.0% of Tween;

the sample diluent: artificial cerebrospinal fluid or artificial serum;

the sample treatment solution is selected from the following solutions: a protein denaturation solution with a pH of 2.0-10.0, 0.05-0.2 mol/L of EDTA (ethylene diamine tetraacetic acid disodium salt) solution with a pH of 4.0-4.8, 0.07-0.2 mol/L of glycine-HCL (glycine-hydrochloric acid) solution with a pH of 2.2-2.8, 0.05-15 mg/mL of pronase with a pH of 8.0-9.0, and 0.01-0.1 mol/L of SDS (sodium dodecyl sulfate) solution with a pH of 8.5-10.0 or 1-8 mol/L of urea with a pH of 7.2-8.0;

the substrate solution comprises TMB (Tetramethylbenzidine), OPD (o-Phenylenediamine), OT (o-Tolidine) and ABTS (2,2'-azino-bis(3-ethylbenzothiazoline-6-sulphonic acid)) or p-NNP (p-Nitrophenyl Phosphate), and preferably the TMB; and the stop solution is 1-20 mol/L of sulfuric acid solution, and preferably 2 mol/L of sulfuric acid solution.

In a specific embodiment of the present invention, the wash concentrate comprises the following components in parts by weight: 96.0 parts of sodium chloride, 2.40 parts of potassium chloride, 42.96 parts of sodium phosphate dibasic dodecahydrate, 2.88 parts of monopotassium phosphate, 0.05 part of Tween-20 and 1000 parts of ultrapure water.

The present invention further provides a preparation method of the GXM antigen immunoassay kit for the *Cryptococcus neoformans* capsular polysaccharide GXM. The preparation method comprises the following specific steps:

(1) Preparing an Enzyme-Labeled Carrier

① diluting GXM with a coating buffer solution to obtain a GXM coating solution, and adding the GXM coating solution into wells of an ELISA plate for coating;

② adding a blocking solution into the wells of the ELISA plate obtained in the step ① for blocking; and ③ removing the blocking solution from the ELISA plate obtained in the step ②, and incubating to obtain a GXM coated enzyme-labeled carrier;

(2) Preparing a GXM Standard Substance diluting a GXM antigen, and preparing the GXM standard substance; and (3) Preparing an Anti-GXM Polyclonal Enzyme-Labeled Antibody Solution An enzyme used for labeling is the horse radish peroxidase, and an anti-GXM polyclonal enzyme-labeled antibody is prepared by a periodate oxidation method; or the enzyme used for labeling is the alkaline phosphatase, and the anti-GXM polyclonal enzyme-labeled antibody is prepared by a glutaraldehyde cross-linking method.

The anti-GXM polyclonal enzyme-labeled antibody is diluted by an enzyme conjugate stabilizer to prepare the anti-GXM polyclonal enzyme-labeled antibody solution. Preferably, the preparation method of the antigen immunoassay kit for the *Cryptococcus neoformans* capsular polysaccharide comprises the following specific steps:

(1) preparing an enzyme-labeled carrier
① diluting GXM to 25-2000 ng/100 μL with a coating buffer solution to obtain a GXM coating solution, adding the GXM coating solution into wells of an ELISA plate, respectively adding 60-200 μL of the coating solution into each well, and coating the ELISA plate at 2-8° C. for 8-16 h;
② adding a blocking solution into the wells of the ELISA plate obtained in the step ①, respectively adding 60-200 μL of the blocking solution into each well, and blocking at 37° C. for 30-90 min; and
③ removing the blocking solution from the ELISA plate obtained in the step ②, and standing at a constant temperature of 37° C. for 30-90 min, thereby obtaining a GXM coated enzyme-labeled carrier;

(2) preparing a GXM standard substance
diluting a GXM antigen into at least 3 different concentrations in a range of 0-100 ng/mL;

(3) preparing an anti-GXM polyclonal enzyme-labeled antibody solution:
an enzyme used for labeling is the horse radish peroxidase, and an anti-GXM polyclonal enzyme-labeled antibody is prepared by a periodate oxidation method; or the enzyme used for labeling is the alkaline phosphatase, and the anti-GXM polyclonal enzyme-labeled antibody is prepared by a glutaraldehyde cross-linking method.

The anti-GXM polyclonal enzyme-labeled antibody is diluted by an enzyme conjugate stabilizer according to a ratio of 1:2000-1:20000 to prepare the anti-GXM polyclonal enzyme-labeled antibody solution;

(4) preparing a sample treatment solution, a wash concentrate, a sample diluent, a substrate solution and a stop solution;

More preferably, the preparation method of the antigen immunoassay kit for the *Cryptococcus neoformans* capsular polysaccharide further comprises:

(5) packaging the anti-GXM polyclonal enzyme-labeled antibody, the GXM standard substance, the sample treatment solution, the wash concentrate, the sample diluent, the substrate solution and the stop solution, and placing the above solutions into a kit box together with a GXM-coated enzyme-labeled antibody and a sealing film.

Preferably, the coating buffer solution is selected from 0.01-0.20 mol/L of PBS (phosphate) buffer solution with a pH of 7.0-8.0, 0.05-0.20 mol/L of CBS (carbonate) buffer solution with a pH of 9.0-9.6 or 0.05 mol/L of Tris(hydroxy methyl aminomethane) buffer solution with a pH of 10.0-10.6.

Preferably, the blocking solution comprises the following component: 0.01-0.20 mol/L of PBS buffer solution with a pH of 7.0-8.0 containing 3-5% of skim milk powder or 1-4% of BSA (Bovine Serum Albumin).

In a specific embodiment of the present invention, the GXM standard substance is prepared by diluting GXM with the sample diluent, and has 5 different concentrations marked as a, b, c, d and e respectively. The concentrations are respectively 100, 32, 10, 6.4 and 3.2 ng/mL.

Another purpose of the present invention is to provide an application of the antigen immunoassay kit for the *Cryptococcus neoformans* capsular polysaccharide in detection of GXM concentrations.

Preferably, the application of the antigen immunoassay kit for the *Cryptococcus neoformans* capsular polysaccharide in detection of GXM concentrations is a competitive ELISA method (one-step method), comprising the following specific steps:

(1) mixing a to-be-detected sample and a sample treatment solution according to a volume ratio of 1:1-5:1, boiling for 1-10 min, and centrifuging to obtain a to-be-detected substance;

(2) uniformly mixing the to-be-detected substance in the step (1) and an anti-GXM polyclonal enzyme-labeled antibody according to an equivalent volume, adding the mixture into a GXM-coated ELISA plate, incubating for 20-60 min, and washing the plate after incubating; and (3) adding 50-100 μL of substrate solution into the ELISA plate in the step (2) for developing, adding the stop solution, and detecting absorbance.

Preferably, the application of the antigen immunoassay kit for the *Cryptococcus neoformans* capsular polysaccharide in detection of GXM concentrations is a competitive ELISA method (two-step method), comprising the following specific steps:

(1) mixing a to-be-detected sample and a sample treatment solution according to a volume ratio of 1:1-5:1, boiling for 1-10 min, and centrifuging to obtain a to-be-detected substance;

(2) uniformly mixing the to-be-detected matter in the step (1) and an anti-GXM polyclonal enzyme-labeled antibody according to an equivalent volume, and incubating for 20-60 min;

(3) adding the mixture in the step (2) into a GXM-coated ELISA plate, incubating for 20-60 min, and washing the plate after incubating; and (4) adding 50-100 μL of substrate solution into the ELISA plate in the step (3) for developing, adding the stop solution, and detecting absorbance.

An appliance principle of the antigen immunoassay kit for the *Cryptococcus neoformans* capsular polysaccharide is as follows:

1) coating GXM onto a solid phase carrier to prepare a solid phase antigen;

2) mixing a treated to-be-detected sample and an anti-GXM polyclonal enzyme-labeled antibody, and reacting at a constant temperature;

3) adding a mixed solution in the step 2) into the solid phase in the 1), and enabling a to-be-detected antigen and a coating antigen to be competitively bound to limited antibody binding sites;

4) carrying out a constant temperature reaction, completely washing, and adding an enzymatic reaction substrate TMB for developing, wherein the color is in negative correlation to GXM concentrations in the to-be-detected sample; and 5) determining absorbance (value A) under a certain wavelength by using a microplate reader, thereby realizing detection of the antigen through a standard curve.

The *Cryptococcus neoformans* adopted in the present invention is purchased from China Pharmaceutical Culture Collection Center.

The capsular polysaccharide monoclonal antibody adopted in the present invention is provided by Dyna (Tianjin) Biological Technology Co., Ltd.

According to the preparation method of the *Cryptococcus neoformans* capsular polysaccharide GXM provided by the present invention, the crude extract of the *Cryptococcus neoformans* capsular polysaccharide GXM is purified by using immunoaffinity chromatography, so that the use of a toxic chemical reagent is effectively avoided, the safety of an operator is ensured, environmental pollution is avoided, specificity is high, and a high-purity *Cryptococcus neoformans* capsular polysaccharide may be prepared while simplifying the preparation process. The prepared GXM is used as an immunogen for producing the polyclonal antibody, and the prepared polyclonal antibody has the characteristics of high titer and excellent specificity, is stable in property and has excellent application prospects. The GXM antigen immunoassay kit is prepared by utilizing the GXM and the anti-GXM polyclonal antibody. The kit adopts a competition method, and the competition method comprises the following steps: coating the GXM onto the ELISA plate at first, enabling the to-be-detected sample or a standard antigen and the coating antigen to be competitively bound with limited antibody binding sites, carrying out a color development reaction with a substrate by virtue of the enzyme, and detecting and calculating to obtain an antigen concentration. The detection kit has good sensitivity, specificity, repeatability and stability, has high recovery rate of a target compound and may provide more accurate and reliable inspection results. The kit is simple and feasible in use and operation, rapid and sensitive in detection and low in price and provides an effective tool for clinical detection of the GXM.

BRIEF DESCRIPTION OF THE DRAWINGS

FIG. 1 is a quantitative detection result of a *Cryptococcus neoformans* capsular polysaccharide GXM provided in the present invention;

FIG. 2 is an HPLC purity analysis result of a *Cryptococcus neoformans* capsular polysaccharide GXM provided in the present invention;

FIG. 3 shows an SDS-PAGE impure protein content analysis result of a *Cryptococcus neoformans* capsular polysaccharide GXM provided in the present invention;

FIG. 4 shows an SDS-PAGE detection result of a rabbit IgG type polyclonal antibody provided in the present invention;

FIG. 5 shows a titer determination result of a rabbit IgG type polyclonal antibody provided in the present invention; and FIG. 6 shows a standard curve graph of a GXM immunoassay kit provided in the present invention.

DETAILED DESCRIPTION OF THE EMBODIMENTS

In order to make purposes, technical means and advantages of the present invention clearly understood, the present invention is further described in detail below in combination with drawings.

The above only describes preferred embodiments of the present invention, not intended to limit a protection scope of the present invention. All modifications, equivalent replacements, improvements and the like made within spirit and principles of the present invention should be included in the protection scope of the present invention.

Embodiment 1

Extraction of a *Cryptococcus neoformans* capsular polysaccharide GXM, comprising the following specific steps:

(1) preparing 0.6 L of YM bouillon culture-medium containing the components of 1.8 g of yeast extract, 3 g of peptone, 1.8 g of maltose extract and 6 g of D-glucose, and culturing *Cryptococcus neoformans*, wherein a culture temperature is 30° C., a shake speed is 200 rpm, and culture time is 36 h;

(2) sterilizing bacterium liquid at 121° C. for 25 min, and centrifuging for 30 min per 16000 g to remove thalli;

(3) slowly adding calcium acetate powder into the supernatant while stirring until a final concentration is 5%, and adding glacial acetic acid to regulate a pH value to be about 5.0; and (4) adding 95% of ethanol in an amount of three times of a volume of the solution into the solution, immediately producing a precipitate, and standing overnight at 4° C.; dumping most of the supernatant, transferring residual substances into 50 mL of round bottom centrifuge tube, centrifuging for 5 min per 12000 g, removing the supernatant, precipitating and drying, thereby obtaining the crude extract of the *Cryptococcus neoformans* capsular polysaccharide GXM.

Embodiment 2

Preparation of an immunoaffinity chromatography column for a *Cryptococcus neoformans* capsular polysaccharide GXM, comprising the following specific steps:

(1) binding a monoclonal antibody of *Cryptococcus neoformans* capsular polysaccharide GXM onto protein A microbeads, mixing the antibody and the protein A into thin homogenate according to the rate that about 2 mg of the monoclonal antibody may be bound to every milliliter of wet microbeads, adding about 1 mL of microbeads into a solution with a total volume of 10 mL, incubating at a room temperature for 1 h, slightly shaking and mixing to be uniform;

(2) washing the microbeads with 0.2 mol/L of sodium borate (pH of 9.0) in an amount of 10 times of the volume for 2 times, and centrifuging for 2 min per 3000 g each time, or centrifuging for 30 s per 10000 g;

(3) resuspending the microbeads with the 0.2 mol/L of sodium borate (pH of 9.0) in an amount of 10 times of the volume, reserving a sample equivalent to 10 mL of the wet microbeads, adding an enough amount of dimethyl heptandilate (solid) into the microbead homogenate to enable a final concentration to be 20 mmol/L, incubating at the room temperature for 30 min, enabling the antibody bound onto the protein A microbeads to be cross-linked with a microbead substrate, slightly mixing to be uniform to obtain a microbead-antibody cross-linked complex, and reserving a sample equivalent to 10 mL of the cross-linked complex;

(4) washing the microbead-antibody cross-linked complex with 0.2 mol/L of ethanol amine (pH of 8.0) once so as to terminate the cross-linking reaction;

(5) resuspending the microbead-antibody cross-linked complex obtained in the step (4) in the 0.2 mol/L of ethanol amine solution, incubating at the room temperature for 2 h, and slightly mixing to be uniform;

(6) washing the microbead-antibody cross-linked complex obtained in the step (5) with PBS, resuspending in the PBS, and adding merthiolate until the final concentration is 0.01% for preserving; and (7) after the microbead-antibody cross-linked complex is successfully cross-linked when detected, filling the microbead-antibody cross-linked complex obtained in the step (6) into a chromatographic column to obtain the immunoaffinity chromatography column for the *Cryptococcus neoformans* capsular polysaccharide, rinsing a container with the PBS, and collecting residual microbeads. If possible, only the antibody microbead substrate needed by the total GXM in a to-be-purified product is used.

Embodiment 3

Purification of the crude extract of the *Cryptococcus neoformans* capsular polysaccharide GXM prepared in Embodiment 1, comprising the following specific steps:

(1) taking the immunoaffinity chromatography column for the *Cryptococcus neoformans* capsular polysaccharide GXM prepared in Embodiment 2, and washing the column with an initial buffer solution in an amount of 20 times of a column bed volume;

(2) adding a to-be-purified sample solution into the chromatography column, enabling the sample solution to flow through the chromatography column according to flow velocity of being about 1 mL/h per milliliter of the column volume, and controlling the flow velocity by a peristaltic pump;

(3) washing the column with a binding buffer solution in an amount of 20 times of the column bed volume;

(4) washing the column with a pre-elution buffer solution in an amount of 20 times of the column bed volume;

(5) adopting stepwise elution, continuously enabling an elution buffer solution in an amount of 0.5 time of the column bed volume to pass through the chromatography column, and collecting each component in different tubes;

(6) detecting content of the GXM in each tube, merging all the tubes with high concentrations, and dialyzing collected antigen eluant according to the purpose of the antigen; and (7) enabling an initial buffer solution in an amount of 20 times of a column bed volume to flow through a substrate, enabling the chromatography column to regenerate, adding 0.01% of merthiolate into the buffer solution, and preserving the chromatography column in an environment of 4° C.

The initial buffer solution, the binding buffer solution, the pre-elution buffer solution and the elution buffer solution are respectively high purity water, a PBS buffer solution with a pH of 7, a carbonate buffer solution with a pH of 9 and 0.1M of glycine buffer solution with a pH of 3.0.

Embodiment 4

Detection of the *Cryptococcus neoformans* capsular polysaccharide GXM prepared in Embodiment 3:

A. Determination of sugar content by a Dubois-sulfuric acid-phenol method, comprising the following specific steps:

(1) weighing 1 g of glucose and dissolving the glucose into 100 mL of $dH_2O$, and preparing 1% of glucose solution;

(2) taking seven 100 mL of clean test tubes, and respectively adding 1 mL of $dH_2O$ and 25 μL of phenol solution into each test tube;

(3) respectively adding 0, 2.5, 5, 10 and 15 μL of glucose solutions and 10 μL of to-be-detected solution into all the test tubes;

(4) slowly adding 2.5 mL of concentrated sulfuric acid into each tube, and uniformly mixing in a unified manner after all the test tubes are filled with the concentrated sulfuric acid;

(5) placing the test tubes in a water bath for about 20 minutes, and cooling to a room temperature;

(6) carefully pouring liquid in each tube into a glass cuvette;

(7) determining an absorbance value under 485 nm by using an ultraviolet spectrophotometer;

(8) drawing a standard curve; and (9) calculating a polysaccharide concentration of the to-be-detected solution according to the standard curve.

The standard curve is shown in FIG. 1, has excellent linearity, and can be used to calculate the concentration of the to-be-detected sample.

B. HPLC purity analysis, comprising the following specific steps:

taking 1 mL of a *Cryptococcus neoformans* capsular polysaccharide GXM sample (3.65 mg/mL)

chromatographic column: Sugar—ParkT72011A09P/N85188Waters mobile phase: ultrapure water flow velocity: 0.5 mL/min column temperature: 85° C.

detector: a differential refraction detector sensitivity setting range: $1.0\times10^{-6}$-$5.0\times10^{-4}$ RIU differential range: 1.00-1.75RIU linear dynamic range: $5\times10^{-3}$-$5\times10^{-9}$RIU noise: $<2\times10^{-8}$RIUATTN HPLC sample injection is detected by the differential refraction detector. A result is shown in FIG. 2. If a single absorption peak appears, it indicates that purity of the sample is good.

C. SDS-PAGE impure protein content analysis, comprising the following specific steps:

(1) preparing SDS-PAGE gel with a concentration of 8%, and making colloid;

(2) adding 10 μL of the *Cryptococcus neoformans* capsular polysaccharide GXM sample prepared in Embodiment 3 into each well;

(3) performing electrophoresis under a constant voltage of 60V for 10 min, then performing electrophoresis under a constant voltage of 120V for about 1 hour, and stopping electrophoresis until a bromophenol blue stripe is 1 cm away from a lower edge of a colloid plate;

(4) staining with Coomassie brilliant blue for 1 hour;

(5) decolorizing overnight at 4° C.; and (6) shooting and observing.

A colloid figure is shown in FIG. 3. By contrast, the *Cryptococcus neoformans* capsular polysaccharide sample prepared in Embodiment 3 has high purity and does not contain any impure protein.

Embodiment 5

Verification of repeatability, recovery rate and stability of an immunoaffinity chromatography column for *Cryptococcus neoformans* capsular polysaccharide GXM:

A. repeatability verification, comprising the following specific steps:

(1) preparing 5 immunoaffinity chromatography columns for the *Cryptococcus neoformans* capsular polysaccharide GXM according to the steps in Embodiment 2, and respectively labeling the chromatography columns as 001, 002, 003, 004 and 005;

(2) taking a crude *Cryptococcus neoformans* capsular polysaccharide GXM prepared in Embodiment 1 as a to-be-purified sample, and uniformly dividing the sample into five parts;

(3) respectively adding the 5 parts of 2 mL of the to-be-purified sample into the 5 chromatography columns in parallel test, and purifying according to the operation in Embodiment 3; and (4) identifying the purified polysaccharide GXM according to the operation in Embodiment 4. Results are as follows:

Quantitative results of the sulfuric acid-phenol method are shown in FIG. 1. Total CV of the purified polysaccharide is less than 10%.

The single absorption peak appears in the HPLC purity analysis.

Any impure protein band does not appear during the SDS-PAGE impure protein content analysis.

TABLE 1

Repeatability verification results of the immunoaffinity chromatography column for the *crytococcus neoformans* capsular polysaccharide GXM

| | Chromatography column number | | | | |
|---|---|---|---|---|---|
| | 001 | 002 | 003 | 004 | 005 |
| Total sugar content | 19.65 | 18.05 | 21.89 | 19.12 | 18.56 |
| Mean value | | | 19.56 | | |
| SD | | | 1.48 | | |
| CV | | | 7.65% | | |

B. recovery verification, comprising the following specific steps:

(1) preparing 5 immunoaffinity chromatography columns for the *Cryptococcus neoformans* capsular polysaccharide GXM according to the steps in Embodiment 2;

(2) taking a *Cryptococcus neoformans* capsular polysaccharide GXM prepared in Embodiment 3 as a purification standard sample with a concentration of 3.65 mg/mL;

(3) respectively adding 2 mL of purification standard sample solution into the 5 chromatography columns in parallel test, and purifying according to the operation in Embodiment 3; and (4) detecting total sugar content of the purified standard sample, wherein results are shown in Table 2, and the recovery rate is calculated to be between 96.5% and 100.5%.

TABLE 2

Recovery rate verification results of the immunoaffinity chromatography column for the *crytococcus neoformans* capsular polysaccharide GXM

| | Chromatography column number | | | | | |
|---|---|---|---|---|---|---|
| | 001 | 002 | 003 | 004 | 005 | Mean value |
| Total sugar content | 7.18 | 7.34 | 7.09 | 7.05 | 7.13 | 7.16 |
| Recovery rate | 98.36% | 100.5% | 97.12% | 96.57% | 97.67% | 98.08% |

C. stability verification, comprising the following specific steps:

(1) preparing 1 immunoaffinity chromatography column for the *Cryptococcus neoformans* capsular polysaccharide GXM according to the steps in Embodiment 2;

(2) taking a *Cryptococcus neoformans* capsular polysaccharide GXM prepared in Embodiment 3 as a purification standard sample with a concentration of 3.65 mg/mL;

(3) adding 1 mL of purification standard sample solution into the chromatography column, purifying according to the operation in Embodiment 3, and performing repetitive sample injection on the same column for 10 times, (regenerating after elution each time); and (4) detecting total sugar content of the purified standard sample after 10 times, wherein results are shown in Table 3, and the recovery rate is calculated to be between 78.08% and 105.80%.

TABLE 3

Stability verification results of the immunoaffinity chromatography column for the *crytococcus neoformans* capsular polysaccharide GXM

| Purification frequency | Total sugar content | Recovery rate |
|---|---|---|
| 1 | 3.47 | 95.10% |
| 2 | 3.64 | 99.70% |
| 3 | 3.86 | 105.80% |
| 4 | 3.32 | 91.00% |
| 5 | 3.57 | 97.80% |
| 6 | 3.12 | 85.50% |
| 7 | 3.45 | 94.50% |
| 8 | 3.01 | 82.50% |
| 9 | 3.05 | 83.60% |
| 10 | 2.85 | 78.08% |
| Mean value | 3.334 | |
| SD | 0.32 | |
| CV | 9.6% | |

It is known from the above results that, the immunoaffinity chromatography column for the *Cryptococcus neoformans* capsular polysaccharide GXM prepared by the steps in Embodiment 2 has extremely high specificity and recovery rate on the target compound, is excellent in the repeatability and the stability, and can achieve the effects of effectively decreasing purification and preparation cost, simplifying preparation steps and increasing preparation efficiency when used in purification and preparation of the *Cryptococcus neoformans* capsular polysaccharide GXM.

Embodiment 6 Biological Activity Contrast of *Cryptococcus neoformans* Capsular Polysaccharide GXM Sample: the *Cryptococcus neoformans* capsular polysaccharide GXM prepared in Embodiment 3

Reference substance: *Cryptococcus neoformans* capsular polysaccharide prepared by a method disclosed in a patent literature CN201110240065.X.

Contrast and verification of the biological activity of the *Cryptococcus neoformans* capsular polysaccharide GXM are performed, comprising the following specific steps:

A. titer verification, comprising the following specific steps:

(1) coating capsular polysaccharide purified in two manners onto an ELISA plate according to 10 ng/well, 25 ng/well, 50 ng/well and 100 g/well;

(2) diluting the HRP-labeled antibody of the monoclonal antibody for the *Cryptococcus neoformans* capsular polysaccharide GXM according to the ratios of 1:2000, 1:4000, 1:8000, 1:16000, 1:32000, 1:64000 and 1:128000, adding the antibody onto the ELISA plate coated by the capsular polysaccharide, and incubating at 37° C. for 60 min;

(3) washing: removing liquid in the ELISA plate wells, adding not less than 300 μL of working washing solution into each well each time, standing for 40 s, patting to be dry, repeating the above washing operation, and washing for 5 times;

(4) developing: adding 50 μL of substrate solution TMB into each well after washing, incubating at 37° C. for 15 min, and keeping out of the sun;

Stopping: adding 50 μL of stop solution into each well, mixing to be uniform, and reading an absorbance value at 450 nm.

Embodiment 7: Preparation of Anti-GXM Polyclonal Antibody

1. Immunizing Animals steps: performing equivalent volume mixing on a GXM antigen and a Freund's complete adjuvant to an appropriate volume, fully emulsifying, performing subcutaneous multi-point injection on New Zealand big ear rabbits, controlling an immunizing dosage of each rabbit to be 0.01-1 mg, collecting ear blood 3 days before immunization, separating serum to perform negative control, and immunizing once every 2 weeks after primary immunization, wherein the method is the same as that in the first time.

TABLE 4

Titer verification results of the *crytococcus neoformans* capsular polysaccharide GXM

| Dilution ratio | Sample | | | | Reference substance | | | |
|---|---|---|---|---|---|---|---|---|
| | 10 ng/well | 25 ng/well | 50 ng/well | 100 ng/well | 10 ng/well | 25 ng/well | 50 ng/well | 100 ng/well |
| blank | 0.050 | 0.048 | 0.047 | 0.051 | 0.052 | 0.045 | 0.046 | 0.049 |
| 1:2000 | 3.630 | 4.000 | 4.000 | 4.000 | 2.163 | 2.562 | 2.782 | 2.941 |
| 1:4000 | 2.976 | 3.976 | 4.000 | 4.000 | 1.082 | 1.281 | 1.391 | 1.471 |
| 1:8000 | 1.815 | 3.750 | 4.000 | 4.000 | 0.541 | 0.641 | 0.696 | 0.735 |
| 1:16000 | 0.908 | 2.287 | 3.218 | 3.462 | 0.270 | 0.320 | 0.348 | 0.368 |
| 1:32000 | 0.454 | 1.143 | 2.516 | 2.767 | 0.135 | 0.160 | 0.174 | 0.184 |
| 1:64000 | 0.227 | 0.572 | 1.258 | 1.384 | 0.068 | 0.080 | 0.087 | 0.092 |
| 1:128000 | 0.113 | 0.286 | 0.629 | 0.692 | 0.034 | 0.040 | 0.043 | 0.040 |

It is known from the above results that, the titer of the sample is obviously higher than that of the latter. It is indicated that, binding capacity between the GXM antigen prepared by the method in the present application and the antibody is far higher than that in the prior art.

B. Verification of biological activity, comprising the following specific steps:

(1) preparing a GXM immunoassay kit;

(2) respectively diluting the sample and the reference substance to be 1000 ng/mL, 500 ng/mL, 200 ng/mL, 100 ng/mL, 50 ng/mL, 20 ng/mL and 10 ng/mL; and (3) detecting by using the GXM immunoassay kit.

TABLE 5

Biological activity verification results of the *crytococcus neoformans* capsular polysaccharide GXM

| Concentration ng/mL | Sample | | Reference substance | |
|---|---|---|---|---|
| | Recovery concentration | Recovery rate | Recovery concentration | Recovery rate |
| 1000 | 1078 | 107.8% | 215.6 | 21.6% |
| 500 | 537 | 107.4% | 107.4 | 21.5% |
| 200 | 228 | 114.0% | 45.6 | 22.8% |
| 100 | 107 | 107.0% | 21.4 | 21.4% |
| 50 | 52 | 104.0% | 10.4 | 20.8% |
| 20 | 25 | 125.0% | 5 | 25.0% |
| 10 | 12 | 120.0% | 2.4 | 24.0% |

It is known from Table 5 that, the recovery rate of the sample is far higher than that of the reference substance.

2. Acquisition of a Polyclonal Antibody 1) titer determination: collecting blood to determine the titer once every a few days during and after immunization, wherein immunization frequency is not less than 3 times; and 2) separating antiserum: collecting lots of blood by using a carotid artery bloodletting method when a serum titer reaches the highest value, centrifuging at a high speed after blood coagulation and serum separation, taking supernatant, and preserving at −20° C.

3. Performing Preliminary Purification by Using a Saturated Ammonium Sulfate Salting-Out Method (1) taking 2 mL of antiserum sample, adding physiological saline of an equivalent volume, then adding 4 mL of saturated ammonium sulfate solution, and precipitating overnight at 4° C.;

(2) centrifuging at low temperature for 10 min per 10000 g, removing the supernatant, dissolving the precipitate with 2 mL of PBS, slowly dripping 1 mL of the saturated ammonium sulfate solution, and standing at 4° C. for 1 hour, and (3) centrifuging at low temperature for 10 min per 10000 g, removing the supernatant, dissolving the precipitate with 1 mL of PBS, and dialyzing overnight at 4° C. with a PBS solution.

4. Further Purifying by Affinity Chromatography Method (1) washing the column with an elution buffer solution (0.01 mol/L of phosphatic buffer solution with a pH of 7.4) in an amount of 5-10 times of a column bed volume;

(2) washing the column with a coupling buffer solution (0.01 mol/L of phosphate buffer solution with a pH of 7.4) in an amount of 5-10 times of the column bed volume;

(3) loading the sample subjected to preliminary purification by using the saturated ammonium sulfate salting-out method;

(4) washing the column with the coupling buffer solution (0.01 mol/L of phosphate buffer solution with the pH of 7.4) in an amount of 5-10 times of the column bed volume; and (5) eluting with an elution buffer solution (a glycine-hydrochloric acid buffer solution with a pH of 2.8) in an amount of 2-5 times of the column bed volume, thereby obtaining the polyclonal antibody resisting the *Cryptococcus neoformans* capsular polysaccharide GXM antigen.

Embodiment 8: Detection of an Anti-GXM Polyclonal Antibody

1. SDS-PAGE Electrophoresis Detection

Figure 4:
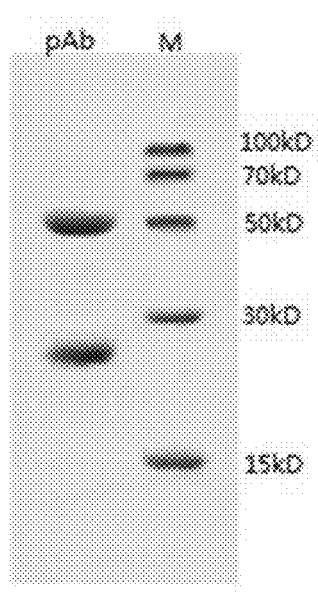

The anti-GXM polyclonal antibody prepared in Embodiment 7 is subjected to SDS-PAGE electrophoresis, and obtained gel is stained with Coomassie brilliant blue. Experimental results are shown in FIG. 4 (a pAb lane is an anti-GXM polyclonal antibody prepared in Embodiment 6, and an M lane is a protein Marker). It can be seen from the figure that, clear bands respectively appear in molecular weight areas of 25 kD and 50 kD and are respectively a hydrocarbon chain and a heavy chain of an antibody protein. Any impure protein band does not appear. It indicates that, the anti-GXM polyclonal antibody prepared in Embodiment 7 has extremely high purity.

2. Titer Determination

Figure 5:
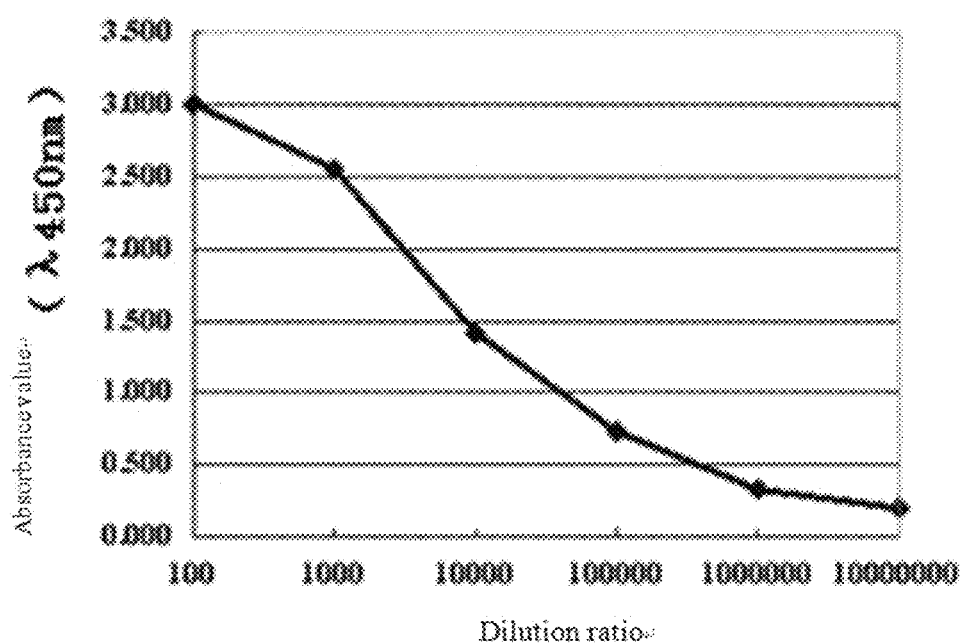

The antibody titer is determined by using an indirect ELISA method. A used secondary enzyme-labeled antibody is horse radish peroxidase-labeled goat anti-rabbit IgC and the negative control is a PBS solution. Detection results are shown in FIG. 5. It can be seen from the results that, the antibody titer is extremely high and is greater than $1:1\times10^6$.

Embodiment 9: Preparation of an Antigen Immunoassay Kit for *Cryptococcus neoformans* Capsular Polysaccharide 1. Preparation of an Enzyme-Labeled Carrier ①  diluting GXM to 25 ng/100 μL with a coating buffer solution to obtain a GXM coating solution, adding the GXM coating solution into wells of an ELISA plate, respectively adding 200 μL of the coating solution into each well, and coating the ELISA plate at 2-8° C. for 8 h;

② adding a blocking solution into the wells of the ELISA plate, respectively adding 200 μL of the blocking solution into each well, and blocking at 37° C. for 30 min; and ③ removing the blocking solution, and standing at a constant temperature of 37° C. for 30 min, thereby obtaining a GXM coated enzyme-labeled carrier.

The coating buffer solution is 0.01 mol/L of PBS buffer solution with a pH of 7.0-7.4.

The prepared blocking solution: 0.01 mol/L of PBS buffer solution with a pH of 7.0-7.4 containing 3% of skim milk powder.

2. Preparation of a GXM Standard Substance

A GXM antigen is diluted into the concentrations of 100, 32, 10, 6.4 and 3.2 ng/mL by using a sample diluent.

3. Preparation of an Anti-GXM Polyclonal Enzyme-Labeled Antibody Solution

An enzyme used for labeling is AP, and preparation of an anti-GXM polyclonal enzyme-labeled antibody is performed by adopting a glutaraldehyde cross-linking method.

The AP-labeled anti-GXM polyclonal enzyme-labeled antibody is diluted by an AP conjugate stabilizer according to a ratio of 1:2000.

4. Preparation of a Sample Treatment Solution, a Wash Concentrate, a Sample Diluent, a Substrate Solution and a Stop Solution the sample treatment solution: dissolving ethylenediamine tetraacetic acid disodium salt with ultrapure water, and preparing into 0.05 mol/L of EDTA solution, wherein a pH value is 4.0-4.8;

the wash concentrate: comprising the following components in parts by weight: 96.0 parts of sodium chloride, 2.40 parts of potassium chloride, 42.96 parts of sodium phosphate dibasic dodecahydrate, 2.88 parts of monopotassium phosphate, 0.05 part of Tween-20 and 1000 parts of ultrapure water;

the sample diluent: artificial serum;

the substrate solution p-NPP solution;

the stop solution: dissolving 54.7 mL of concentrated sulfuric acid into high purity water and diluting to 100 mL, thereby obtaining 10 mol/L of sulfuric acid solution.

5. The anti-GXM polyclonal enzyme-labeled antibody, the GXM standard substance, the sample treatment solution, the wash concentrate, the sample diluent, the substrate solution and the stop solution are respectively filled into corresponding reagent bottles; the reagent bottles are fixed by a sponge carrier and are placed into a kit body with a GXM-coated enzyme-labeled antibody and a sealing film together.

Embodiment 10: Preparation of an Antigen Immunoassay Kit for *Cryptococcus neoformans* Capsular Polysaccharide In a GXM coating solution, the GXM is diluted to 25 ng/100 μL with 0.1 mol/L of PBS buffer solution with a pH of 7.6-8.0, and the rest steps are the same as those in Embodiment 9.

Embodiment 11: Preparation of an Antigen Immunoassay Kit for *Cryptococcus neoformans* Capsular Polysaccharide In a GXM coating solution, the GXM is diluted to 25 ng/100 μL with 0.2 mol/L of PBS buffer solution with a pH of 7.6-8.0, and the rest steps are the same as those in Embodiment 9.

Embodiment 12: Preparation of an Antigen Immunoassay Kit for *Cryptococcus neoformans* Capsular Polysaccharide In a GXM coating solution, the GXM is diluted to 25 ng/100 μL with 0.05 mol/L of CBS buffer solution with a pH of 9.0-9.6, and the rest steps are the same as those in Embodiment 9.

Embodiment 13: Preparation of an Antigen Immunoassay Kit for *Cryptococcus neoformans* Capsular Polysaccharide In a GXM coating solution, the GXM is diluted to 25 ng/100 μL with 0.1 mol/L of CBS buffer solution with a pH of 9.0-9.6, and the rest steps are the same as those in Embodiment 9.

Embodiment 14: Preparation of an Antigen Immunoassay Kit for *Cryptococcus neoformans* Capsular Polysaccharide In a GXM coating solution, the GXM is diluted to 25 ng/100 μL with 0.2 mol/L of CBS buffer solution with a pH of 9.0-9.6, and the rest steps are the same as those in Embodiment 9.

Embodiment 15: Preparation of an Antigen Immunoassay Kit for a *Cryptococcus neoformans* Capsular Polysaccharide In a GXM coating solution, the GXM is diluted to 25 ng/100 μL with 0.05 mol/L of Tris buffer solution with a pH of 10.0-10.6, and the rest steps are the same as those in Embodiment 9.

Embodiment 16: Preparation of an Antigen Immunoassay Kit for *Cryptococcus neoformans* Capsular Polysaccharide 1. Preparation of an Enzyme-Labeled Carrier ① diluting GXM to 500 ng/100 μL with a coating buffer solution to obtain a GXM coating solution, adding the GXM coating solution into wells of an ELISA plate, respectively adding 100 μL of the coating solution into each well, and coating the ELISA plate at 2-8° C. for 12 h;

② adding a blocking solution into the wells of the ELISA plate, respectively adding 100 μL of the blocking solution into each well, and blocking at 37° C. for 60 min; and ③ removing the blocking solution, and standing at a constant temperature of 37° C. for 60 min, thereby obtaining a GXM coated enzyme-labeled carrier.

The coating buffer solution is 0.01 mol/L of PBS buffer solution with a pH of 7.2-7.4.

The prepared blocking solution 0.01 mol/L of PBS buffer solution with a pH of 7.2-7.4 containing 4% of skim milk powder.

2. Preparation of a GXM Standard Substance

A GXM antigen is diluted into the concentrations of 100, 32, 10, 6.4 and 3.2 ng/mL by using a sample diluent.

3. Preparation of an Anti-GXM Polyclonal Enzyme-Labeled Antibody Solution

An enzyme used for labeling is HRP, and preparation of an anti-GXM polyclonal enzyme-labeled antibody is performed by adopting a periodate oxidation method.

The HRP-labeled anti-GXM polyclonal enzyme-labeled antibody is diluted by an HRP conjugate stabilizer according to a ratio of 1:10000.

4. Preparation of a Sample Treatment Solution, a Wash Concentrate, a Sample Diluent, a Substrate Solution and a Stop Solution the sample treatment solution: dissolving ethylenediamine tetraacetic acid disodium salt with ultrapure water, and preparing into 0.1 mol/L of EDTA solution, wherein a pH value is 4.0-4.8;

the wash concentrate: comprising the following components in parts by weight: 96.0 parts of sodium chloride, 2.40 parts of potassium chloride, 42.96 parts of sodium phosphate dibasic dodecahydrate, 2.88 parts of monopotassium phosphate, 0.05 part of Tween-20 and 1000 parts of ultrapure water;

the sample diluent: artificial cerebrospinal fluid;

the substrate solution: TMB solution;

the stop solution: diluting concentrated sulfuric acid and ultrapure water according to a volume ratio of 1:8, thereby obtaining 2 mol/L of sulfuric acid solution.

5. The anti-GXM polyclonal enzyme-labeled antibody, the GXM standard substance, the sample treatment solution, the wash concentrate, the sample diluent, the substrate solution and the stop solution are respectively filled into corresponding reagent bottles; the reagent bottles are fixed by a sponge carrier and are placed into a kit body with a GXM-coated enzyme-labeled antibody and a sealing film together.

Embodiment 17: Preparation of an Antigen Immunoassay Kit for *Cryptococcus neoformans* Capsular Polysaccharide The blocking solution is 0.2 mol/L of PBS buffer solution with a pH of 7.6-8.0 containing 5% of skim milk powder, and the rest steps are the same as those in Embodiment 16.

Embodiment 18: Preparation of an Antigen Immunoassay Kit for *Cryptococcus neoformans* Capsular Polysaccharide The blocking solution is 0.2 mol/L of PBS buffer solution with a pH of 7.6-8.0 containing 1% of BSA, and the rest steps are the same as those in Embodiment 16.

Embodiment 19: Preparation of an Antigen Immunoassay Kit for *Cryptococcus neoformans* Capsular Polysaccharide The blocking solution is 0.2 mol/L of PBS buffer solution with a pH of 7.6-8.0 containing 2% of BSA, and the rest steps are the same as those in Embodiment 16.

Embodiment 20: Preparation of an Antigen Immunoassay Kit for *Cryptococcus neoformans* Capsular Polysaccharide The blocking solution is 0.2 mol/L of PBS buffer solution with a pH of 7.6-8.0 containing 4% of BSA, and the rest steps are the same as those in Embodiment 16.

Embodiment 21: Preparation of an Antigen Immunoassay Kit for *Cryptococcus neoformans* Capsular Polysaccharide 1. Preparation of an Enzyme-Labeled Carrier ① diluting GXM to 2 μg/100 μL with a coating buffer solution to obtain a GXM coating solution, adding the GXM coating solution into wells of an ELISA plate, respectively adding 60 μL of the coating solution into each well, and coating the ELISA plate at 2-8° C. for 16 h;

② adding a blocking solution into the wells of the ELISA plate, respectively adding 60 μL of the blocking solution into each well, and blocking at 37° C. for 90 min; and ③ removing the blocking solution, and standing at a constant temperature of 37° C. for 90 min, thereby obtaining a GXM coated enzyme-labeled carrier.

The coating buffer solution is 0.1 mol/L of PBS buffer solution with a pH of 7.4 (comprising the following components in parts by weight: 4.25 parts of sodium chloride, 15.40 parts of sodium phosphate dibasic dodecahydrate, 0.95 part of monopotassium phosphate and 500 parts of ultrapure water).

The prepared blocking solution: 0.1 mol/L of PBS buffer solution with a pH of 7.2-7.4 containing 4% of BSA.

2. Preparation of a GXM Standard Substance

A GXM antigen is diluted into the concentrations of 100, 32, 10, 6.4 and 3.2 ng/mL by using a sample diluent.

3. Preparation of an Anti-GXM Polyclonal Enzyme-Labeled Antibody Solution

An enzyme used for labeling is HRP, and preparation of an anti-GXM polyclonal enzyme-labeled antibody is performed by adopting a periodate oxidation method.

The HRP-labeled anti-GXM polyclonal enzyme-labeled antibody is diluted by an HRP conjugate stabilizer according to a ratio of 1:20000.

4. Preparation of a Sample Treatment Solution, a Wash Concentrate, a Sample Diluent, a Substrate Solution and a Stop Solution the sample treatment solution: dissolving ethylenediamine tetraacetic acid disodium salt with ultrapure water, and preparing into a 0.2 mol/L of EDTA solution, wherein a pH value is 4.0-4.8;

the wash concentrate: comprising the following components in parts by weight: 96.0 parts of sodium chloride, 2.40 parts of potassium chloride, 42.96 parts of sodium phosphate dibasic dodecahydrate, 2.88 parts of monopotassium phosphate, 0.05 part of Tween-20 and 1000 parts of ultrapure water;

the sample diluent: artificial serum;

the substrate solution: TMB solution;

the stop solution: 98% of concentrated sulfuric acid.

5. The anti-GXM polyclonal enzyme-labeled antibody, the GXM standard substance, the sample treatment solution, the wash concentrate, the sample diluent, the substrate solution and the stop solution are respectively filled into corresponding reagent bottles; the reagent bottles are fixed by a sponge carrier and are placed into a kit body with a GXM-coated enzyme-labeled antibody and a sealing film together.

Embodiment 22: Preparation of an Antigen Immunoassay Kit for *Cryptococcus neoformans* Capsular Polysaccharide A preparation method of a sample treatment solution comprises the steps: dissolving sodium dodecyl sulfate with ultrapure water, preparing 0.01 mol/L of SDS solution with a pH of 8.5-10.0, and performing the rest steps which are the same as those in Embodiment 21.

Embodiment 23: Preparation of an Antigen Immunoassay Kit for *Cryptococcus neoformans* Capsular Polysaccharide A preparation method of a sample treatment solution comprises the steps: dissolving sodium dodecyl sulfate with ultrapure water, preparing 0.05 mol/L of SDS solution with a pH of 8.5-10.0, and performing the rest steps which are the same as those in Embodiment 21.

Embodiment 24: Preparation of an Antigen Immunoassay Kit for *Cryptococcus neoformans* Capsular Polysaccharide A preparation method of a sample treatment solution comprises the steps: dissolving sodium dodecyl sulfate with ultrapure water, preparing 0.1 mol/L of SDS solution with a pH of 8.5-10.0, and performing the rest steps which are the same as those in Embodiment 21.

Embodiment 25: Preparation of an Antigen Immunoassay Kit for *Cryptococcus neoformans* Capsular Polysaccharide A preparation method of a sample treatment solution comprises the steps: dissolving glycine with ultrapure water, preparing 0.07 mol/L of glycine solution, regulating a pH to 2.2-2.8 with a concentrated HCL solution, and performing the rest steps which are the same as those in Embodiment 21.

Embodiment 26: Preparation of an Antigen Immunoassay Kit for *Cryptococcus neoformans* Capsular Polysaccharide A preparation method of a sample treatment solution comprises the steps: dissolving glycine with ultrapure water, preparing 0.13 mol/L of glycine solution, regulating a pH to 2.2-2.8 with a concentrated HCL solution, and performing the rest steps which are the same as those in Embodiment 21.

Embodiment 27: Preparation of an Antigen Immunoassay Kit for *Cryptococcus neoformans* Capsular Polysaccharide A preparation method of a sample treatment solution comprises the steps: dissolving glycine with ultrapure water, preparing 0.2 mol/L of glycine solution, regulating a pH to 2.2-2.8 with a concentrated HCL solution, and performing the rest steps which are the same as those in Embodiment 21.

Embodiment 28: Preparation of an Antigen Immunoassay Kit for *Cryptococcus neoformans* Capsular Polysaccharide A preparation method of a sample treatment solution comprises the steps: dissolving pronase with ultrapure water, preparing 0.05 mg/mL of pronase solution. A pH value of the pronase solution is 8.0-9.0, and the rest steps are the same as those in Embodiment 21.

Embodiment 29: Preparation of an Antigen Immunoassay Kit for *Cryptococcus neoformans* Capsular Polysaccharide A preparation method of a sample treatment solution comprises the steps: dissolving pronase with ultrapure water, preparing 5 mg/mL of pronase solution. A pH value of the pronase solution is 8.0-9.0, and the rest steps are the same as those in Embodiment 21.

Embodiment 30: Preparation of an Antigen Immunoassay Kit for *Cryptococcus neoformans* Capsular Polysaccharide A preparation method of a sample treatment solution comprises the steps: dissolving pronase with ultrapure water, preparing 15 mg/mL of pronase solution. A pH value of the pronase solution is 8.0-9.0, and the rest steps are the same as those in Embodiment 21.

Embodiment 31: Preparation of an Antigen Immunoassay Kit for *Cryptococcus neoformans* Capsular Polysaccharide A preparation method of a sample treatment solution comprises the steps: dissolving urea with ultrapure water, and preparing 1 mol/L of urea. A pH value of the urea is 7.2-8.0, and the rest steps are the same as those in Embodiment 21.

Embodiment 32: Preparation of an Antigen Immunoassay Kit for *Cryptococcus neoformans* Capsular Polysaccharide A preparation method of a sample treatment solution comprises the steps: dissolving urea with ultrapure water, and preparing 4 mol/L of urea. A pH value of the urea is 7.2-8.0, and the rest steps are the same as those in Embodiment 21.

Embodiment 33: Preparation of an Antigen Immunoassay Kit for *Cryptococcus neoformans* Capsular Polysaccharide A preparation method of a sample treatment solution comprises the steps: dissolving urea with ultrapure water, and preparing 8 mol/L of urea. A pH value of the urea is 7.2-8.0, and the rest steps are the same as those in Embodiment 21.

Embodiment 34: Operating Steps of a GXM Immunoassay Kit

1. Sample Treatment 1) mixing a to-be-detected sample and a sample treatment solution according to a volume ratio of 1:1, and adding the mixture into a boiling water bath for 1 min;

2) centrifuging 1000 g of mixed solution after the water bath for 1 min; and 3) detecting by using a supernatant after centrifuging.

2. Detection Steps 1) taking the antigen immunoassay kit for the *Cryptococcus neoformans* capsular polysaccharide prepared in Embodiments 9-15, and taking out an antigen-coated enzyme-labeled carrier;

2) preparing a working washing solution: diluting a wash concentrate by 20 times (adding 19 parts of sterile deionized water or ultrapure water into 1 part of the wash concentrate);

3) sample mixing: respectively setting a standard curve group and a to-be-detected sample group, wherein
the standard curve group: each standard curve paint (3.2, 6.4, 10, 32 and 100 ng/mL)
the to-be-detected sample group: to-be-detected samples treated in the step 1 are repeatedly detected by 10 times;
respectively performing equivalent volume mixing on the two groups and a GXM enzyme-labeled antibody, and incubating at 37° C. for 20 min;

4) sample transfer: transferring a mixed solution in the step 3) into ELISA plate wells, adding 60 μL of the mixed solution into each well, and incubating at 37° C. for 20 min;

5) washing: removing liquid from the ELISA plate wells, adding not less than 300 μL of the working washing solution into each well each time, standing for 40 s, patting to be dry, repeating the above washing operation, and totally washing for 5 times;

6) developing: adding 60 μL of a substrate solution p-NPP into each well after washing, incubating at 37° C. for 15 min, and keeping out of the sun;

7) stopping: adding 50 μL of stop solution into each well, mixing to be uniform, and reading an absorbance value at 405 nm; and 8) result judgment: respectively inputting determined absorbance values of the standard solution and the to-be-detected samples into a computer, calculating concentration values of the GXM in each to-be-detected sample according to semi-logarithmic standard curves and equations drawn by calculation software and the absorbance values of the to-be-detected samples, calculating CV values, and comparing repeatability of samples detected by each kit.

TABLE 6

Sample detection results of kits prepared in Embodiments 9-15

|  | Detection kit | Embodiment 9 | Embodiment 10 | Embodiment 11 | Embodiment 12 | Embodiment 13 | Embodiment 14 | Embodiment 15 |
|---|---|---|---|---|---|---|---|---|
| Antigen concentration of standard curve (μg/L) | 3.2 | 1.208 | 1.329 | 1.170 | 1.244 | 1.276 | 1.160 | 1.276 |
|  | 6.4 | 1.169 | 1.285 | 1.131 | 1.204 | 1.234 | 1.122 | 1.235 |
|  | 10 | 1.083 | 1.191 | 1.048 | 1.115 | 1.143 | 1.040 | 1.144 |
|  | 32 | 0.776 | 0.853 | 0.751 | 0.799 | 0.819 | 0.745 | 0.819 |
|  | 100 | 0.406 | 0.447 | 0.393 | 0.418 | 0.429 | 0.390 | 0.429 |
| To-be-detected sample | OD$_{450}$ | 0.864 | 0.948 | 0.819 | 0.894 | 0.904 | 0.797 | 0.903 |
|  |  | 0.869 | 0.931 | 0.825 | 0.878 | 0.908 | 0.847 | 0.905 |
|  |  | 0.865 | 0.939 | 0.809 | 0.870 | 0.934 | 0.817 | 0.896 |
|  |  | 0.852 | 0.942 | 0.835 | 0.890 | 0.901 | 0.833 | 0.926 |
|  |  | 0.817 | 0.942 | 0.812 | 0.874 | 0.910 | 0.794 | 0.865 |
|  |  | 0.897 | 0.949 | 0.827 | 0.929 | 0.891 | 0.822 | 0.903 |
|  |  | 0.844 | 0.932 | 0.860 | 0.884 | 0.911 | 0.824 | 0.892 |
|  |  | 0.879 | 0.954 | 0.829 | 0.912 | 0.894 | 0.814 | 0.904 |
|  |  | 0.854 | 0.932 | 0.832 | 0.895 | 0.916 | 0.811 | 0.897 |
|  |  | 0.852 | 0.924 | 0.814 | 0.893 | 0.938 | 0.824 | 0.916 |
|  | Antigen concentration (μg/L) | 24.57 | 24.69 | 25.90 | 24.22 | 25.12 | 27.24 | 25.22 |
|  |  | 24.17 | 25.83 | 25.45 | 25.38 | 24.84 | 23.18 | 25.08 |
|  |  | 24.48 | 25.28 | 26.77 | 26.00 | 22.95 | 25.52 | 25.75 |
|  |  | 25.48 | 25.07 | 24.61 | 24.51 | 25.31 | 24.28 | 23.55 |
|  |  | 28.32 | 25.05 | 26.49 | 25.69 | 24.67 | 27.48 | 28.11 |
|  |  | 22.13 | 24.62 | 25.29 | 21.73 | 26.09 | 25.16 | 25.24 |
|  |  | 26.06 | 25.76 | 22.66 | 24.93 | 24.60 | 24.96 | 26.05 |
|  |  | 23.41 | 24.25 | 25.09 | 22.96 | 25.88 | 25.83 | 25.12 |
|  |  | 25.34 | 25.81 | 24.87 | 24.13 | 24.23 | 26.05 | 25.68 |
|  |  | 25.46 | 26.36 | 26.28 | 24.26 | 22.70 | 25.00 | 24.26 |
|  | CV % | 6.6% | 2.6% | 4.7% | 5.3% | 4.5% | 5.0% | 4.7% |

Detection results of the kits prepared in Embodiments 9-15 for the same sample are shown in Table 4. It can be seen from data in Table 6 that, the CV value of each kit for the sample detection results is less than 7%, which indicates that the dispersion degree of each kit for the sample detection results is low and repeatability is good so the kit can be used in immunodetection of the *Cryptococcus neoformans* capsular polysaccharide antigen; and moreover, the CV value detected by the kit prepared in Embodiment 10 is the lowest, which is 2.6%, which indicates that the kit has the best detection repeatability in the test of the present embodiment.

Embodiment 35: Operating Steps of a GXM Immunoassay Kit

1. Sample Treatment 1) mixing a to-be-detected sample and a sample treatment solution according to a volume ratio of 3:1, and adding the mixture into a boiling water bath for 5 min;

2) centrifuging 5000 g of mixed solution after the water bath for 5 min; and 3) detecting by using a supernatant after centrifuging.

2. Detection Steps 1) taking the antigen immunoassay kit for the *Cryptococcus neoformans* capsular polysaccharide prepared in Embodiments 16-20, and taking out an antigen-coated enzyme-labeled carrier;

2) preparing a working washing solution: diluting a wash concentrate by 20 times (adding 19 parts of sterile deionized water or ultrapure water into 1 part of the wash concentrate);

3) sample mixing: respectively setting a standard curve group and a to-be-detected sample group, wherein the standard curve group: each standard curve point (3.2, 6.4, 10, 32 and 100 ng/mL)

the to-be-detected sample group: to-be-detected samples treated are repeatedly detected by 10 times;

respectively performing equivalent volume mixing on the two groups and a GXM enzyme-labeled antibody, and incubating at 37° C. for 40 min;

4) sample transfer: transferring a mixed solution in the step 3) into ELISA plate wells, adding 80 µL of the mixed solution into each well, and incubating at 37° C. for 40 min;

5) washing: removing liquid in the ELISA plate wells, adding not less than 300 µL of the working washing solution into each well each time, standing for 40 s, patting dry, repeating the above washing operation, and totally washing for 5 times;

6) developing: adding 80 µL of substrate solution into each well after washing, incubating at 37° C. for 15 min, and keeping out of the sun;

7) stopping: adding 50 µL of a stop solution into each well, mixing to be uniform, and reading an absorbance value at 450 nm; and 8) result judgment: respectively inputting determined absorbance values of the standard solution and the to-be-detected samples into a computer, calculating concentration values of the GXM in each to-be-detected sample according to semi-logarithmic standard curves and equations drawn by calculation software and the absorbance values of the to-be-detected samples, calculating CV values, and comparing repeatability of samples detected by each kit.

TABLE 7

Sample detection results of kits prepared in Embodiments 16-20

| | Detection kit | Embodiment 16 | Embodiment 17 | Embodiment 18 | Embodiment 19 | Embodiment 20 |
|---|---|---|---|---|---|---|
| Antigen concentration of standard curve (µg/L) | 3.2 | 1.206 | 1.326 | 1.167 | 1.242 | 1.273 |
| | 6.4 | 1.166 | 1.283 | 1.129 | 1.201 | 1.232 |
| | 10 | 1.081 | 1.189 | 1.046 | 1.113 | 1.141 |
| | 32 | 0.774 | 0.852 | 0.750 | 0.797 | 0.817 |
| | 100 | 0.405 | 0.446 | 0.392 | 0.417 | 0.428 |
| To-be-detected sample | $OD_{450}$ | 0.852 | 0.948 | 0.818 | 0.882 | 0.910 |
| | | 0.851 | 0.959 | 0.856 | 0.903 | 0.910 |
| | | 0.843 | 0.939 | 0.826 | 0.870 | 0.895 |
| | | 0.863 | 0.987 | 0.835 | 0.894 | 0.908 |
| | | 0.854 | 0.917 | 0.836 | 0.887 | 0.910 |
| | | 0.867 | 0.950 | 0.805 | 0.871 | 0.899 |
| | | 0.852 | 0.927 | 0.825 | 0.852 | 0.909 |
| | | 0.857 | 0.932 | 0.832 | 0.872 | 0.913 |
| | | 0.846 | 0.923 | 0.831 | 0.890 | 0.891 |
| | | 0.859 | 0.940 | 0.813 | 0.891 | 0.936 |
| | Antigen concentration (µg/L) | 25.31 | 24.56 | 25.90 | 24.98 | 24.54 |
| | | 25.36 | 23.80 | 22.90 | 23.43 | 24.50 |
| | | 26.03 | 25.23 | 25.25 | 25.89 | 25.62 |
| | | 24.44 | 21.95 | 24.52 | 24.06 | 24.67 |
| | | 25.17 | 26.77 | 24.45 | 24.56 | 24.54 |
| | | 24.16 | 24.42 | 27.00 | 25.78 | 25.36 |
| | | 25.33 | 26.08 | 25.32 | 27.29 | 24.60 |
| | | 24.90 | 25.68 | 24.80 | 25.71 | 24.30 |
| | | 25.76 | 26.37 | 24.87 | 24.35 | 25.90 |
| | | 24.74 | 25.15 | 26.28 | 24.26 | 22.70 |
| | CV % | 2.3% | 5.7% | 4.5% | 4.5% | 3.6% |

Detection results of the kits prepared in Embodiments 16-20 for the same sample are shown in Table 7. It can be seen from data in Table 7 that, the CV value of each kit for the sample detection results is less than 6%, which indicates that the dispersion degree of each kit for the sample detection results is low and repeatability is good so the kit can be used in immunodetection of the *Cryptococcus neoformans* capsular polysaccharide antigen; and moreover, the CV value detected by the kit prepared in Embodiment 16 is the lowest, which is 2.3%, which indicates that the kit has the best detection repeatability in the test of the present embodiment.

Embodiment 36: Operating Steps of a GXM Immunoassay Kit

1. Sample Treatment 1) mixing a to-be-detected sample and a sample treatment solution according to a volume ratio of 5:1, and adding the mixture into a boiling water bath for 10 min;

2) centrifuging 10000 g of a mixed solution after the water bath for 10 min; and 3) detecting by using a supernatant after centrifuging.

2. Detection Steps 1) taking the antigen immunoassay kit for the *Cryptococcus neoformans* capsular polysaccharide prepared in Embodiments 21-33, and taking out an antigen-coated enzyme-labeled carrier;

2) preparing a working washing solution: diluting a wash concentrate by 20 times (adding 19 parts of sterile deionized water or ultrapure water into 1 part of the wash concentrate);

3) sample mixing: respectively setting a standard curve group and a to-be-detected sample group, wherein the standard curve group: each standard curve point (3.2, 6.4, 10, 32 and 100 ng/mL)

the to-be-detected sample group: to-be-detected samples treated are repeatedly detected by 10 times;

respectively performing equivalent volume mixing on the two groups and a GXM enzyme-labeled antibody, and incubating at 37° C. for 60 min;

4) sample transfer: transferring a mixed solution in the step 3) into ELISA plate wells, adding 100 μL of the mixed solution into each well, and incubating at 37° C. for 60 min;

5) washing: removing liquid from the ELISA plate wells, adding not less than 300 μL of the working washing solution into each well each time, standing for 40 s, patting to be dry, repeating the above washing operation, and totally washing for 5 times;

6) developing: adding 100 μL of a substrate solution into each well after washing, incubating at 37° C. for 15 min, and keeping out of the sun;

7) stopping: adding 50 μL of stop solution into each well, mixing to be uniform, and reading an absorbance value at 450 nm; and 8) result judgment: respectively inputting determined absorbance values of the standard solution and the to-be-detected samples into a computer, calculating concentration values of the GXM in each to-be-detected sample according to semi-logarithmic standard curves and equations drawn by calculation software and the absorbance values of the to-be-detected samples, calculating CV values, and comparing repeatability of samples detected by each kit.

TABLE 8-1

Sample detection results of kits prepared in Embodiments 21-27

| | Detection kit | Embodiment 21 | Embodiment 22 | Embodiment 23 | Embodiment 24 | Embodiment 25 | Embodiment 26 | Embodiment 27 |
|---|---|---|---|---|---|---|---|---|
| Antigen concentration of standard curve (μg/L) | 3.2 | 1.242 | 1.366 | 1.202 | 1.279 | 1.311 | 1.244 | 1.369 |
| | 6.4 | 1.201 | 1.321 | 1.163 | 1.237 | 1.268 | 1.204 | 1.324 |
| | 10 | 1.113 | 1.224 | 1.078 | 1.146 | 1.175 | 1.115 | 1.227 |
| | 32 | 0.797 | 0.877 | 0.772 | 0.821 | 0.842 | 0.799 | 0.879 |
| | 100 | 0.417 | 0.459 | 0.404 | 0.43 | 0.441 | 0.418 | 0.46 |
| To-be-detected sample | OD$_{450}$ | 0.861 | 0.968 | 0.856 | 0.889 | 0.937 | 0.885 | 0.952 |
| | | 0.879 | 0.929 | 0.864 | 0.91 | 0.938 | 0.893 | 0.982 |
| | | 0.882 | 0.955 | 0.863 | 0.911 | 0.922 | 0.873 | 0.958 |
| | | 0.867 | 0.974 | 0.824 | 0.922 | 0.936 | 0.895 | 1.019 |
| | | 0.89 | 0.981 | 0.867 | 0.924 | 0.942 | 0.863 | 0.971 |
| | | 0.863 | 0.961 | 0.857 | 0.905 | 0.902 | 0.879 | 0.956 |
| | | 0.879 | 0.981 | 0.841 | 0.916 | 0.947 | 0.883 | 0.971 |
| | | 0.883 | 0.951 | 0.857 | 0.914 | 0.914 | 0.883 | 0.955 |
| | | 0.875 | 0.978 | 0.858 | 0.901 | 0.93 | 0.884 | 0.98 |
| | | 0.915 | 0.963 | 0.838 | 0.888 | 0.964 | 0.885 | 0.958 |
| | Antigen concentration (μg/L) | 26.59 | 25.13 | 24.84 | 26.42 | 24.54 | 24.88 | 26.41 |
| | | 25.14 | 27.87 | 24.23 | 24.83 | 24.5 | 24.33 | 24.3 |
| | | 24.98 | 26 | 24.27 | 24.73 | 25.62 | 25.8 | 25.93 |
| | | 26.06 | 24.7 | 27.38 | 23.95 | 24.67 | 24.14 | 21.91 |
| | | 24.39 | 24.27 | 23.96 | 23.84 | 24.19 | 26.58 | 25.04 |
| | | 26.38 | 25.59 | 24.77 | 25.21 | 27.11 | 25.31 | 26.1 |
| | | 25.21 | 24.28 | 26 | 24.4 | 23.9 | 25.07 | 25.03 |
| | | 24.9 | 26.3 | 24.76 | 24.57 | 26.25 | 25.02 | 26.14 |
| | | 25.49 | 24.46 | 24.7 | 25.52 | 25.09 | 24.95 | 24.43 |
| | | 22.59 | 25.47 | 26.24 | 26.47 | 22.7 | 24.89 | 25.98 |
| | CV % | 4.5% | 4.4% | 4.3% | 3.7% | 5.0% | 2.8% | 5.4% |

TABLE 8-2

Sample detection results of kits prepared in Embodiments 28-33

|  |  | Deletion kit | Embodiment 28 | Embodiment 29 | Embodiment 30 | Embodiment 31 | Embodiment 32 | Embodiment 33 |
|---|---|---|---|---|---|---|---|---|
| Antigen concentration of standard curve (μg/L) | | 3.2 | 1.205 | 1.282 | 1.314 | 1.195 | 1.314 | 1.407 |
| | | 6.4 | 1.165 | 1.24 | 1.271 | 1.156 | 1.272 | 1.361 |
| | | 10 | 1.08 | 1.149 | 1.178 | 1.071 | 1.178 | 1.261 |
| | | 32 | 0.774 | 0.823 | 0.844 | 0.767 | 0.844 | 0.903 |
| | | 100 | 0.405 | 0.431 | 0.442 | 0.402 | 0.442 | 0.473 |
| To-be-detected sample | $OD_{450}$ | | 0.856 | 0.902 | 0.929 | 0.849 | 0.909 | 0.988 |
| | | | 0.854 | 0.905 | 0.939 | 0.849 | 0.936 | 0.984 |
| | | | 0.859 | 0.922 | 0.901 | 0.835 | 0.96 | 0.978 |
| | | | 0.87 | 0.913 | 0.965 | 0.819 | 0.972 | 1 |
| | | | 0.841 | 0.912 | 0.956 | 0.856 | 0.92 | 0.985 |
| | | | 0.867 | 0.895 | 0.926 | 0.859 | 0.937 | 1.001 |
| | | | 0.855 | 0.896 | 0.921 | 0.866 | 0.942 | 1.015 |
| | | | 0.838 | 0.901 | 0.958 | 0.826 | 0.949 | 0.977 |
| | | | 0.839 | 0.935 | 0.959 | 0.85 | 0.925 | 0.999 |
| | | | 0.845 | 0.925 | 0.915 | 0.829 | 0.95 | 0.998 |
| | Antigen concentration (μg/L) | | 24.99 | 25.62 | 25.28 | 24.95 | 26.76 | 25.7 |
| | | | 25.17 | 25.38 | 24.56 | 24.92 | 24.82 | 25.99 |
| | | | 24.71 | 24.11 | 27.38 | 26.04 | 23.15 | 26.38 |
| | | | 23.92 | 24.81 | 22.79 | 27.32 | 22.36 | 24.89 |
| | | | 26.19 | 24.83 | 23.39 | 24.38 | 25.93 | 25.9 |
| | | | 24.1 | 26.08 | 25.49 | 24.15 | 24.76 | 24.82 |
| | | | 25.02 | 26.03 | 25.87 | 23.64 | 24.4 | 23.94 |
| | | | 26.37 | 25.64 | 23.31 | 26.76 | 23.93 | 26.44 |
| | | | 26.32 | 23.2 | 23.24 | 24.89 | 25.58 | 24.98 |
| | | | 25.86 | 23.95 | 26.33 | 26.49 | 23.84 | 25.01 |
| | CV % | | 3.5% | 3.9% | 6.3% | 4.8% | 5.4% | 3.2% |

Detection results of the kits prepared in Embodiments 21-33 for the same sample are shown in Table 8. It can be seen from data in Table 8 that, the CV value of each kit for the sample detection results is less than 7%, which indicates that the dispersion degree of each kit for the sample detection results is low and repeatability is good so the kit can be used in immunodetection of the *Cryptococcus neoformans* capsular polysaccharide antigen; and moreover, the CV value detected by the kit prepared in Embodiment 26 is the lowest, which is 2.8%, which indicates that the kit has the best detection repeatability in the test of the present embodiment.

Embodiment 37: A Clinical Application of a GXM Immunoassay Kit

Figure 6:
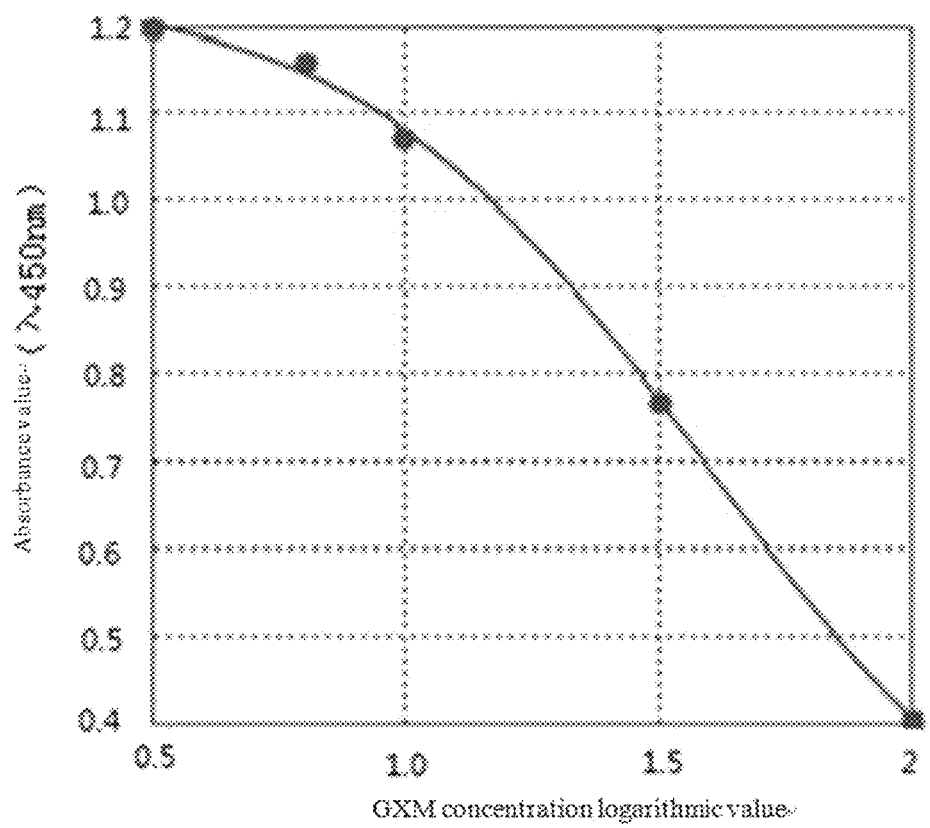

1. Drawing a Standard Curve steps: taking a kit prepared in Embodiment 16, obtaining a measured value of each of standard curve points (3.2, 6.4, 10, 32 and 100 ng/mL) shown in Table 9 according to steps in Embodiment 35, and making a standard curve shown in FIG. 6 by utilizing data in Table 9 and taking a logarithmic value of concentrations of a GXM antigen in a sample as a horizontal axis (x axis) and taking an absorbance value measured at 450 nm as a vertical axis (y axis), thereby obtaining a standard curve equation:

$$y = A + (B-A)/[1 + e^{(-a*x+b)}]$$

wherein A=1.24414;

B=0.14362;

a=2.92462;

b=4.66878.

Linear correlation $R^2 = 0.99946$, and the standard curve equation is fitted well.

2. Determination of a Reference Value of the GXM Immunoassay Kit steps: taking 30 positive samples which are clinically diagnosed to be infected with *cryptococcus*, taking 200 normal human samples, centrifuging the samples, diluting and performing other treatments, determining $OD_{450}$ value according to steps in Embodiment 30 by utilizing the kit prepared in Embodiment 11, and calculating antigen concentration values shown in Table 10 according to the standard curve equation and absorbance values of the samples;

calculating and detecting antigen concentrations according to results of the standard curve; by detecting the 200 normal human samples, taking an antigen concentration value in a 95% confidence interval as a Cut-off upper limit: $\bar{x}$ (mean)+2 s(standard deviation)=5.46+2*2.3=10; by detecting 30 positive patients, taking an antigen concentration value in the 95% confidence interval as a Cut-off lower limit: $\bar{x}$ (mean)−2 s(standard deviation)=23.15−2*8.57=6; and determining a patient with the antigen concentration value of 6 ng/ml-10 ng/ml as a suspected patient, thereby obtaining a judgment standard reference value of the GXM immunoassay kit shown in Table 11.

TABLE 9

Detected standard curve

| Antigen concentration of standard substance (ng/mL) | $OD_{450}$ |
|---|---|
| 3.2 | 1.196 |
| 6.4 | 1.157 |
| 10 | 1.072 |
| 32 | 0.768 |
| 100 | 0.402 |

TABLE 10

ELISA clinical detection results of the GXM immunoassay kit

| Groups | Cases | GXM concentration $\bar{x} \pm s$(ng/mL) | Positive rate (%) |
|---|---|---|---|
| Normal person | 200 | 5.46 ± 2.3 | 3.5 (7/200) |
| Positive patient | 30 | 23.15 ± 8.57 | 93* (28/30) |

Note:
*represents that P < 0.01 compared with normal persons.

TABLE 11

Judgment standard reference value of the GXM immunoassay kit

| Positive | Suspected | Negative |
|---|---|---|
| Antigen concentration ≥10 ng/mL | 6 ng/mL ≤ antigen concentration ≤10 ng/mL | Antigen concentration ≤6 ng/mL |

If the sample detection result is in the suspected interval, second detection shall be performed to determine the result.

Embodiment 38: Methodology Examination of a GXM Immunoassay Kit

1. Sensitivity Experiment steps: taking a kit prepared in Embodiment 19, and detecting 20 clinically diagnosed samples according to steps in Embodiment 34.

Diagnostic sensitivity is equal to a detected case number of positive samples/a total case number of the positive samples×100%. Experimental results are shown in Table 12. It can be seen from data in Table 12 that, the sensitivity of the GXM immunoassay kit used in the present experiment is higher than 85%.

TABLE 12

Experimental resuts of sensitivity detection

| No. | OD$_{450}$ | Calculated antigen concentration (µg/L) | Judged Result |
|---|---|---|---|
| 1 | 0.053 | 1684.51 | positive |
| 2 | 0.061 | 1290.67 | positive |
| 3 | 0.09 | 701.97 | positive |
| 4 | 0.135 | 408.85 | positive |
| 5 | 0.227 | 213.34 | positive |
| 6 | 0.418 | 95.07 | positive |
| 7 | 0.319 | 137.96 | positive |
| 8 | 1.007 | 13.15 | positive |
| 9 | 0.103 | 582.55 | positive |
| 10 | 0.164 | 319.93 | positive |
| 11 | 0.313 | 141.46 | positive |
| 12 | 0.063 | 1219.78 | positive |
| 13 | 0.342 | 125.72 | positive |
| 14 | 0.533 | 65.41 | positive |
| 15 | 1.122 | 6.56 | suspected |
| 16 | 0.062 | 1254.21 | positive |
| 17 | 1.013 | 12.78 | positive |
| 18 | 1.049 | 10.62 | suspected |
| 19 | 0.126 | 446.65 | positive |
| 20 | 1.08 | 8.85 | suspected |

2. Specificity Experiment steps: taking a kit prepared in Embodiment 19, and detecting 20 healthy human samples according to steps in Embodiment 35.

Specificity is equal to a detected case number of negative samples/a total case number of the negative samples×100%.

Experimental results are shown in Table 13. It can be seen from data in Table 13 that, the sensitivity of the GXM immunoassay kit used in the present experiment is higher than 90%.

TABLE 13

Experimental results of specificity detection

| No. | OD$_{450}$ | Calculated antigen concentration (µg/L) | Judged Result |
|---|---|---|---|
| 1 | 1.391 | Lower than lower detection limit | Negative |
| 2 | 1.253 | Lower than lower detection limit | Negative |
| 3 | 1.211 | 1.99 | Negative |
| 4 | 1.328 | Lower than lower detection limit | Negative |
| 5 | 1.346 | Lower than lower detection limit | Negative |
| 6 | 1.320 | Lower than lower detection limit | Negative |
| 7 | 1.125 | 6.40 | Suspected |
| 8 | 1.309 | Lower than lower detection limit | Negative |
| 9 | 1.289 | Lower than lower detection limit | Negative |
| 10 | 1.318 | Lower than lower detection limit | Negative |
| 11 | 1.269 | Lower than lower detection limit | Negative |
| 12 | 1.303 | Lower than lower detection limit | Negative |
| 13 | 1.247 | 0.09 | Negative |
| 14 | 1.296 | Lower than lower detection limit | Negative |
| 15 | 1.474 | Lower than lower detection limit | Negative |
| 16 | 1.304 | Lower than lower detection limit | Negative |
| 17 | 1.267 | Lower than lower detection limit | Negative |
| 18 | 1.350 | Lower than lower detection limit | Negative |
| 19 | 1.270 | Lower than lower detection limit | Negative |
| 20 | 1.330 | Lower than lower detection limit | Negative |

3. Recovery Rate Experiment steps: selecting normal human blood, respectively adding 90 µg/L and 30 µg/L of *Cryptococcus neoformans* capsular polysaccharide antigen, detecting an antigen concentration according to steps in Embodiment 35 by utilizing the kit prepared in Embodiment 19, and calculating a ratio between a true value and an expected value, thereby obtaining the recovery rate. The kit is qualified if the recovery rate is between 80% and 120%. Experimental results are shown in Table 14. It can be seen from data in Table 14 that, the recovery rate of the GXM immunoassay kit used in the present experiment is between 80% and 120%, and the recovery rate is good.

TABLE 14

Experimental results of the recovery rate

| | OD$_{450}$ | Calculated antigen concentration (µg/L) | Recovery rate |
|---|---|---|---|
| Concentration of added antigen is 90 µg/L | 0.419 | 105 | 114% |
| | 0.475 | 90 | 97% |
| | 0.447 | 100 | 104% |

TABLE 14-continued

Experimental results of the recovery rate

| | OD$_{450}$ | Calculated antigen concentration (μg/L) | Recovery rate |
|---|---|---|---|
| Concentration of added antigen is 30 μg/L | 0.902 | 25 | 84% |
| | 0.895 | 28 | 90% |
| | 0.899 | 27 | 87% |

4. Repeatability Experiment

1) Between-Run Precision

An acceptable quality level: testing the same sample once per day for 10 consecutive workdays according to steps in Embodiment 35 by utilizing the kits prepared in Embodiments 18 and 19, calculating a mean value M, a standard deviation SD and a variable coefficient CV, wherein the sample is qualified if the variable coefficient CV is less than or equal to 25%. Experimental results are shown in Table 15. It can be concluded from data in Table 15 that, the between-run precision (that is, the variable coefficient CV) of the GXM immunoassay kit provided in the present invention is 15%, is less than 25% and conforms to the standard.

TABLE 15

Experimental results of the between-run precision
Summarized between-run precision

| Workday (d) | Calculated antigen concentration (μg/L) |
|---|---|
| 1 | 30.11 |
| 2 | 29.09 |
| 3 | 22.80 |
| 4 | 19.01 |
| 5 | 29.63 |
| 6 | 27.39 |
| 7 | 20.81 |
| 8 | 23.82 |
| 9 | 27.41 |
| 10 | 26.49 |
| M | 25.66 |
| SD | 3.85 |
| CV | 15% |

2) Within-Run Precision

An acceptable quality level: testing 10 groups of data of the same sample in parallel in the same batch of experiments; determining twice each time; taking a mean value; calculating a corresponding antigen concentration; and calculating a mean value M, a standard deviation SD and a variable coefficient CV, wherein the sample is qualified if the variable coefficient CV is less than or equal to 15%. The within-run precision (that is, the variable coefficient CV) of the GXM immunoassay kit provided in the present invention is 7%, is less than 15% and conforms to the standard.

TABLE 16

Experimental results of the within-run precision

| No. | OD$_{450}$-1 | OD$_{450}$-2 | OD$_{450}$ | Calculated antign concentration (μg/L) |
|---|---|---|---|---|
| 1 | 0.792 | 0.807 | 0.8 | 28.87 |
| 2 | 0.769 | 0.780 | 0.775 | 31.27 |
| 3 | 0.839 | 0.856 | 0.848 | 24.62 |
| 4 | 0.813 | 0.819 | 0.816 | 27.40 |
| 5 | 0.794 | 0.822 | 0.808 | 28.13 |
| 6 | 0.802 | 0.822 | 0.812 | 27.76 |
| 7 | 0.816 | 0.863 | 0.84 | 25.29 |
| 8 | 0.781 | 0.812 | 0.797 | 29.15 |
| 9 | 0.817 | 0.828 | 0.823 | 26.77 |
| 10 | 0.770 | 0.798 | 0.784 | 30.39 |
| M | | | | 28.0 |
| SD | | | | 2.1 |
| CV | | | | 7% |

5. Stability Experiment steps: placing the GXM immunoassay kit prepared in Embodiment 18 in an environment of 37° C.; and detecting a standard quality control solution (55 μg/L) with a known concentration through a standard curve per day for consecutive 5 days, wherein if variation of the detected value (that is, a variable coefficient CV) is less than 20%, the kit is proved to be stable. Experimental results are shown in Table 17. It can be seen from data in Table 17 that, the variable coefficient CV of the GXM immunoassay kit prepared in Embodiment 8 adopted in the present experiment within 5 days is less than or equal to 20%, which indicates that the GXM immunoassay kit provided in the present invention is good in stability.

TABLE 17

Experimental results of the stability

| | | 1 | 2 | 3 | 4 | 5 | CV |
|---|---|---|---|---|---|---|---|
| | Blank | 0.056 | 0.060 | 0.060 | 0.050 | 0.061 | |
| Antigen concentration of standard curve (μg/L) | 3.2 | 1.176 | 1.216 | 1.121 | 1.201 | 1.198 | |
| | 6.4 | 1.156 | 1.157 | 1.108 | 1.099 | 1.108 | |
| | 10 | 1.037 | 1.107 | 1.086 | 1.084 | 1.079 | |
| | 32 | 0.771 | 0.764 | 0.767 | 0.752 | 0.772 | |
| | 100 | 0.403 | 0.4 | 0.399 | 0.391 | 0.402 | |
| Standard quality control point | OD$_{450}$ | 0.587 | 0.598 | 0.576 | 0.581 | 0.563 | |
| | Antigen concentration (μg/L) | 55.447 | 50.297 | 48.989 | 53.497 | 60.380 | 8% |

What is claimed is:

1. A preparation method of *Cryptococcus neoformans* capsular polysaccharide glucuronoxylomannan (GXM), comprising:

performing crude extraction on *Cryptococcus neoformans* capsular polysaccharide GXM;

preparing an immunoaffinity chromatography column for the *Cryptococcus neoformans* capsular polysaccharide GXM; and purifying a crude extract of the *Cryptococcus neoformans* capsular polysaccharide GXM by utilizing the GXM immunoaffinity chromatography column; and, the immunoaffinity chromatography column is prepared through following steps:

(1) dissolving a monoclonal antibody of *Cryptococcus neoformans* capsular polysaccharide GXM in a solution, and mixing the monoclonal antibody with an affinity chromatography substrate to form thin homogenate;

(2) washing the homogenate obtained in the step (1) with a cross-linking buffer solution, and centrifuging to obtain a mixture of the antibody and the affinity chromatography substrate;

(3) resuspending the mixture of the antibody and the affinity chromatography substrate obtained in step (2) with the cross-linking buffer solution, adding a difunctional binding agent into the obtained suspension, incubating, uniformly mixing, and separating the liquid from the solid to obtain an affinity chromatography substrate-antibody conjugated complex;

(4) washing the affinity chromatography substrate-antibody conjugated complex obtained in the step (3) with a blocking solution;

(5) resuspending the affinity chromatography substrate-antibody conjugated complex obtained in the step (4) in the blocking solution, incubating, and uniformly mixing; and (6) packing: filling the affinity chromatography substrate-antibody conjugated complex obtained in the step (5) into a chromatographic column, thereby obtaining the immunoaffinity chromatography column for the *Cryptococcus neoformans* capsular polysaccharide GXM; wherein, the affinity chromatography substrate-antibody conjugated complex obtained in step (5) is subjected to a preservative treatment and then filled into the chromatography column, and the preservative treatment comprises following steps: washing the affinity chromatography substrate-antibody conjugated complex obtained in the step (5) with a PBS buffer solution, resuspending the complex in the PBS buffer solution, and adding merthiolate for preservation.

2. The preparation method according to claim 1, wherein the extraction of the *Cryptococcus neoformans* capsular polysaccharide GXM comprises the following steps: (1) culturing *Cryptococcus neoformans* until a bacteria concentration reaches a later logarithmic phase; (2) performing autoclaved sterilization on bacterium liquid, centrifuging to remove thalli, and reserving supernatant; (3) adding calcium acetate powder into the supernatant while stirring until the final concentration of the supernatant is 2-8%, and adding glacial acetic acid to regulate the pH value to be 4.6-5.2; and (4) adding ethanol with a concentration of 90-98% into the solution obtained in the step (3), standing overnight at 4° C., centrifuging, removing the supernatant, drying and precipitating, thereby obtaining the crude extract of the *Cryptococcus neoformans* capsular polysaccharide GXM.

3. The preparation method according to claim 1, wherein the step of purifying the crude extract of the *Cryptococcus neoformans* capsular polysaccharide GXM by utilizing the GXM immunoaffinity chromatography column comprises the following steps: (1) rinsing the GXM immunoaffinity chromatography column by utilizing a buffer solution which is the same as a to-be-purified sample solution; (2) enabling the to-be-purified sample solution to flow through the chromatography column treated in the step (1); (3) washing the column with a binding buffer solution; (4) washing the column with a pre-elution buffer solution; (5) performing stepwise elution, continuously enabling an elution buffer solution to flow through the chromatography column, and collecting each component in different tubes; and (6) detecting the content of the GXM in each tube, and merging all the tubes with high concentrations.

4. The preparation method according to claim 3, wherein flow velocity of the to-be-purified sample in the step (2) is 0.5-1.5 mL/h.

5. The preparation method according to claim 3, wherein the binding buffer solution in the step (3) is selected from one of a PBS buffer solution, a Tris-HCl buffer solution and an acetic acid-sodium acetate buffer solution, and the use amount of the binding buffer solution is 10-25 times of the column bed volume; and/or the pre-elution buffer solution in the step (4) is a carbonate buffer solution, and the use amount of the pre-elution buffer solution is 10-25 times of the column bed volume; and/or the elution buffer solution in the step (5) is selected from 0.1M glycine buffer solution with a pH of 3.0, a citrate-phosphate buffer solution with a pH of 3.0, a citrate-sodium citrate buffer solution with a pH of 3.0 and an acetate-sodium acetate buffer solution with a pH of 3.0, and the use amount of the elution buffer solution is 0.4-0.8 of the column bed volume.

6. The preparation method according to claim 1, wherein the affinity chromatography substrate in the step (1) is selected from protein A microbeads, protein G microbeads and active microbeads; and/or the solution in the step (1) is selected from a carbonate buffer solution and an acetic acid-sodium acetate buffer solution; and/or a ratio of the affinity chromatography substrate to the solution in the step (1) is as follows: 0.5-2.0 mL of the affinity chromatography substrate is added into every 10 mL of the solution; and a ratio of the affinity chromatography substrate to the antibody is as follows: every 1 mL of the affinity chromatography substrate is bound to 1-4 mg of the monoclonal antibody.

7. The preparation method according to claim 1, wherein the cross-linking buffer solution in the step (2) is a 0.1-0.3 mol/L of sodium borate solution with a pH value of 8.0-9.5, and the use amount of the buffer solution is 5-15 times of the volume of the affinity chromatography substrate; and/or the cross-linking buffer solution in the step (3) is a sodium borate solution with a concentration of 0.1-0.3 mol/L and a pH value of 8.3-9.5, and the use amount is 5-15 times of the volume of the affinity chromatography substrate.

8. The preparation method according to claim 1, wherein the difunctional binding agent in the step (3) is selected from dimethyl heptandilate, carbonyldimidazole, cyanogen bromide, hydroxysuccinimide and acetyl iodine, and the use amount is as follows: the final concentration of the binding agent in the suspension is 15-25 mmol/L.

9. The preparation method according to claim 1, wherein the blocking solution in the steps (4) and (5) is selected from ethanol amine and aminoethane solutions.

10. The preparation method according to claim 1, wherein, the preparing an immunoaffinity chromatography column further comprises:

(7) preserving the affinity chromatography substrate-antibody conjugated complex obtained in step (6) or packed immunoaffinity chromatography column for the *Cryptococcus neoformans* capsular polysaccharide GXM obtained in step (6) under a condition of 4° C., and enabling a performance to be stable within 1 year.

11. The preparation method according to claim 10, wherein, the preparing an immunoaffinity chromatography column further comprises a step (8) of regeneration: washing and regenerating the chromatography column preserved under the condition of 4° C. in the step (7) or the used chromatography column with a buffer solution which has a solvent the same as a to-be-purified sample, in an amount of 10-25 times of the volume of the column bed before use.

12. The preparation method according to claim 1, wherein, a concentration of the merthiolate is 0.005-0.015%.

* * * * *